(12) United States Patent
Takahashi et al.

(10) Patent No.: US 11,730,912 B2
(45) Date of Patent: Aug. 22, 2023

(54) HYDROGEN SUPPLY APPARATUS AND HYDROGEN SUPPLY SYSTEM

(71) Applicant: Panasonic Intellectual Property Management Co., Ltd., Osaka (JP)

(72) Inventors: Yasufumi Takahashi, Osaka (JP); Kazuhito Hato, Osaka (JP); Kunihiro Ukai, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 860 days.

(21) Appl. No.: 16/779,693

(22) Filed: Feb. 3, 2020

(65) Prior Publication Data

US 2020/0171265 A1 Jun. 4, 2020

Related U.S. Application Data

(63) Continuation of application No. PCT/JP2018/030935, filed on Aug. 22, 2018.

(30) Foreign Application Priority Data

Sep. 27, 2017 (JP) .................................. 2017-186904

(51) Int. Cl.
*A61M 16/12* (2006.01)
*A61M 16/10* (2006.01)
*A61G 10/02* (2006.01)

(52) U.S. Cl.
CPC ........... *A61M 16/122* (2014.02); *A61G 10/02* (2013.01); *A61M 16/107* (2014.02);
(Continued)

(58) Field of Classification Search
CPC .. A61M 16/10–125; A61M 16/12–127; A61M 2202/0266; A61M 16/0087; A61H 33/14
See application file for complete search history.

(56) References Cited

U.S. PATENT DOCUMENTS

| 10,546,469 B2 * | 1/2020 | Peterson | ................ H05B 45/20 |
| 2010/0006099 A1 * | 1/2010 | Murota | ................ A61G 10/00 |
| | | | 128/205.26 |

(Continued)

FOREIGN PATENT DOCUMENTS

| CN | 101516317 A | 8/2009 |
| CN | 205144968 U | 4/2016 |

(Continued)

OTHER PUBLICATIONS

English Translation of Chinese Search Report dated Mar. 1, 2021 for the related Chinese Patent Application No. 201880031622.7.
(Continued)

*Primary Examiner* — Joseph D. Boecker
*Assistant Examiner* — Thomas W Greig
(74) *Attorney, Agent, or Firm* — McDermott Will & Emery LLP

(57) ABSTRACT

A hydrogen supply apparatus includes: an air path having an inlet and an outlet; a fan that is disposed in the air path and produces a flow of air from the inlet to the outlet; a first pipe having an end that forms a first supply port through which to supply hydrogen gas to the air path; a flow control device that is attached to the first pipe and adjusts a flow rate of the hydrogen gas; and a hydrogen gas sensor, disposed downstream of the fan or the end in a direction of flow of the air that detects a concentration of the hydrogen gas in the air path, where the end is disposed between the fan and the outlet or between the fan and the inlet in the air path.

20 Claims, 12 Drawing Sheets

(52) U.S. Cl.
CPC ......... *A61M 16/12* (2013.01); *A61M 2202/02* (2013.01); *A61M 2202/0266* (2013.01); *A61M 2205/13* (2013.01); *A61M 2205/3303* (2013.01); *A61M 2205/3334* (2013.01); *A61M 2205/3368* (2013.01)

(56) References Cited

U.S. PATENT DOCUMENTS

| | | | |
|---|---|---|---|
| 2013/0008438 A1* | 1/2013 | Sugawara | A61M 16/101 128/202.24 |
| 2014/0378745 A1* | 12/2014 | Lin | A61M 16/16 600/27 |
| 2015/0101601 A1* | 4/2015 | Lin | C25B 15/08 128/202.26 |
| 2015/0292091 A1* | 10/2015 | Satoh | C25B 15/08 204/265 |
| 2017/0165447 A1* | 6/2017 | Dasse | A61K 33/00 |
| 2018/0028774 A1* | 2/2018 | Lin | C25B 1/04 |
| 2018/0320274 A1* | 11/2018 | Lin | C02F 1/4618 |
| 2019/0062932 A1* | 2/2019 | Lin | C02F 1/008 |

FOREIGN PATENT DOCUMENTS

| | | |
|---|---|---|
| JP | 2000-140043 A | 5/2000 |
| JP | 2012-075744 | 4/2012 |
| JP | 2012-102924 A | 5/2012 |
| JP | 2016-114260 A | 6/2016 |
| JP | 2017-032273 A | 2/2017 |
| JP | 2017-218333 A | 12/2017 |
| WO | 2008/013163 | 1/2008 |

OTHER PUBLICATIONS

International Search Report of PCT application No. PCT/JP2018/030935 dated Oct. 30, 2018.

"Hydrogen gas inhalation therapy (No. 51)" on item "Advanced Medical Care B" of "Senshin Iryo no Kaku Gijutsu no Gaiyou [Overview of Technologies for Advanced Medical Care]", [online], Sep. 1, 2017, Ministry of Health, Labour and Welfare, Japan, [searched on Sep. 15, 2017], Internet <URL: http://www.mhlw.go.jp/topics/bukyoku/isei/sensiniryo/kikan03.html>.

* cited by examiner

HYDROGEN SUPPLY APPARATUS AND HYDROGEN SUPPLY SYSTEM

BACKGROUND

1. Technical Field

The present disclosure relates to a hydrogen supply apparatus and a hydrogen supply system.

2. Description of the Related Art

In recent years, attention has been focused on a medical technology with which to take hydrogen gas into the body in addition to drinking of water containing hydrogen. For example, a brief overview of "hydrogen gas inhalation therapies" is provided in item "Advanced Medical Care B" of "Senshin Iryo no Kaku Gijutsu [Overview of Technologies for Advanced Medical Care]", [online], Sep. 1, 2017, Ministry of Health, Labour and Welfare, [searched on Sep. 15, 2017], Internet <URL: http://www.mhlw.go.jp/topics/bukyoku/isei/sensiniryo/kikan03.html>.

Further, as shown in FIG. 13, International Publication No. 2008/013163 discloses a hydrogen supply system 300. The hydrogen supply system 300 supplies hydrogen from a hydrogen supplier 302 to an interior 303 through a hydrogen supply pipe 304. In addition, the hydrogen supply system 300 includes a hydrogen stirrer 305 and has a function of preventing hydrogen from being unevenly distributed in the interior 303. Furthermore, the hydrogen supply system 300 includes a sensor 306, a controller 307, an on-off valve 308, and an vent 309.

The sensor 306 is attached above or around the interior 303. The sensor 306 measures the concentration of hydrogen in the interior 303. The controller 307 is connected to the sensor 306 by a circuit or the like and coordinates with the sensor 306. The on-off valve 308 is provided inside the hydrogen supply pipe 304 and coordinates with the sensor 306 via the controller 307. When a concentration of hydrogen as measured by the sensor 306 exceeds a certain value, the on-off valve 308 is actuated by the controller 307, so that the amount of hydrogen that is supplied from the hydrogen supplier 302 to the interior 303 through the hydrogen supply pipe 304 is controlled. When an amount of hydrogen in the interior 303 as measured by the sensor 306 exceeds a certain value, the vent 309 is actuated by the controller 307, so that air containing hydrogen in the interior 303 is exhausted to an exterior 310.

SUMMARY

The technologies disclosed in "Senshin Iryo no Kaku Gijutsu [Overview of Technologies for Advanced Medical Care]", [online], Sep. 1, 2017, Ministry of Health, Labour and Welfare, [searched on Sep. 15, 2017], Internet <URL: http://www.mhlw.go.jp/topics/bukyoku/isei/sensiniryo/kikan03.html> and International Publication No. 2008/013163 give no through to the supply of a mixture of hydrogen gas and outdoor air to an interior. One non-limiting and exemplary embodiment provides a technology that can supply a mixture of hydrogen gas and outdoor air to an interior and that is advantageous to assuring a high level of safety.

In one general aspect, the techniques disclosed here feature a hydrogen supply apparatus including: an air path having an inlet and an outlet; a fan that is disposed in the air path and produces a flow of air from the inlet to the outlet; a first pipe having an end that forms a first supply port through which to supply hydrogen gas to the air path; a flow control device that is attached to the first pipe and adjusts a flow rate of the hydrogen gas; and a hydrogen gas sensor, disposed downstream of the fan or the end in a direction of flow of the air that detects a concentration of the hydrogen gas in the air path, where the end is disposed between the fan and the outlet or between the fan and the inlet in the air path.

The hydrogen supply apparatus can supply a mixture of hydrogen gas and outdoor air to an interior and is advantageous to assuring a high level of safety.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
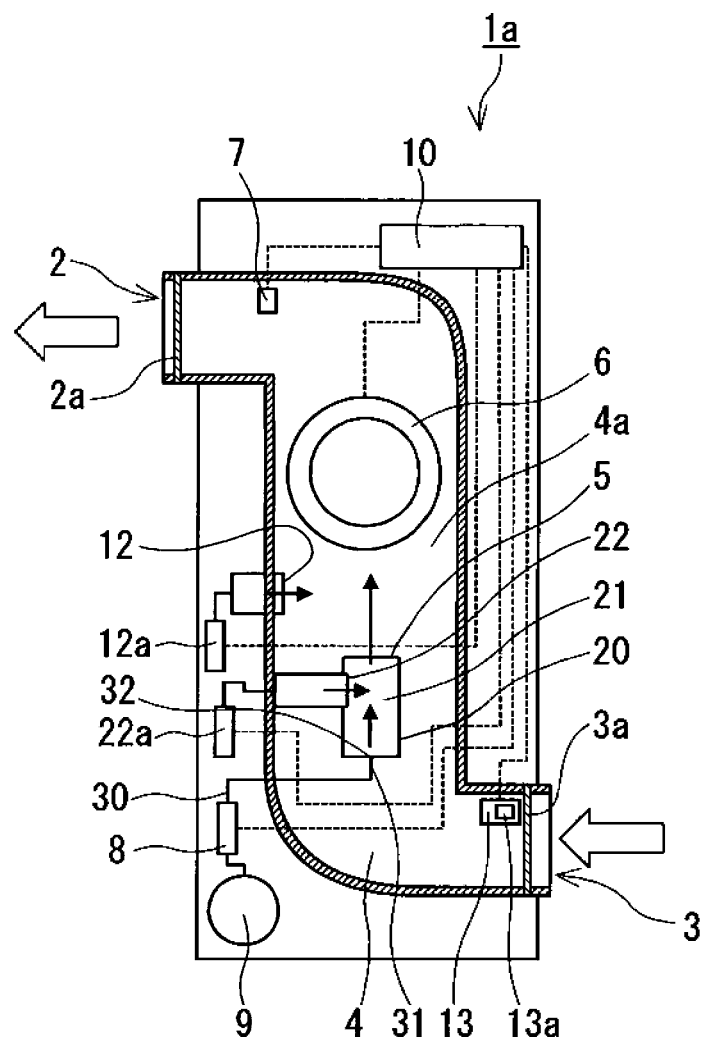
FIG. 1 is a diagram schematically showing an example of a hydrogen supply apparatus of the present disclosure.

Underlying Knowledge Forming Basis of the Present Disclosure

A method for taking hydrogen into the body by drinking of water containing hydrogen has such a problem that only a minute amount of hydrogen can be taken in, as only a minute amount of hydrogen gas can dissolve in water. For a higher intake of hydrogen, it is conceivable that hydrogen gas may be supplied to an interior as in the case of the hydrogen supply system 300 disclosed in International Publication No. 2008/013163. Meanwhile, no attempt has been made to supply a mixture of hydrogen gas and outdoor air to an interior on a daily basis.

It is necessary that a concentration of hydrogen gas in air be kept lower than a lower explosion limit. In the hydrogen supply system 300 disclosed in International Publication No. 2008/013163, a concentration of hydrogen is measured above or around the interior 303 by the sensor 306; however, a mixture of hydrogen gas and other gases in the hydrogen supply pipe 304 is not suggested, so that there is a possibility that a high concentration of hydrogen gas may be supplied through the hydrogen supply pipe 304. In this case, there is a possibility that there may appear a space in the interior 303 near the hydrogen supply pipe 304 where a concentration of hydrogen exceeds the lower explosion limit and falls within an explosive range. For this reason, the technology disclosed in International Publication No. 2008/013163 leaves room for improvement in safety.

In view of the foregoing circumstances, the inventor devised a hydrogen supply apparatus of the present disclosure by diligently studying a technology that can supply a mixture of hydrogen gas and outdoor air to an interior and that is advantageous to assuring a high level of safety.

In a first aspect of the present disclosure, there is provided a hydrogen supply apparatus including: an air path having an inlet and an outlet; a fan that is disposed in the air path and produces a flow of air from the inlet to the outlet; a first pipe having an end that forms a first supply port through which to supply hydrogen gas to the air path; a flow control device that is attached to the first pipe and adjusts a flow rate of the hydrogen gas; and a hydrogen gas sensor, disposed downstream of the fan or the end in a direction of flow of the air that detects a concentration of the hydrogen gas in the air path, where the end is disposed between the fan and the outlet or between the fan and the inlet in the air path.

According to the first aspect, the supply of hydrogen gas to the air path through the first supply port makes it possible to supply the interior with a mixture of hydrogen gas and air taken into the air path from the exterior. In addition, since the flow rate of hydrogen gas that is supplied to the air path can be adjusted by the flow control device, the concentration of hydrogen gas in the air path can be adjusted to fall within a desired range based on a lower explosion limit of hydrogen gas in air. For this reason, the hydrogen supply apparatus according to the first aspect is advantageous to assuring a high level of safety.

In a second aspect of the present disclosure, there is provided the hydrogen supply apparatus according to the first aspect, further including a hydrogen gas sensor, disposed downstream of the end in a direction of flow of the air in the air path, that detects a concentration of the hydrogen gas in the air path. According to the second aspect, the concentration of hydrogen gas in the air path can be detected by the hydrogen gas sensor, and a result of the detection can be utilized so that the concentration of hydrogen gas in the air path is adjusted to fall within a predetermined range. For this reason, the hydrogen supply apparatus according to the second aspect is more advantageous to assuring a high level of safety.

In a third aspect of the present disclosure, there is provided the hydrogen supply apparatus according to the first or second aspect, further including a controller that controls the flow control device to keep a concentration of hydrogen gas at the outlet lower than a predetermined concentration. According to the third aspect, the control of the flow control device by the controller keeps the concentration of hydrogen gas at the outlet lower than a predetermined concentration based on a lower explosion limit of hydrogen gas in air. As a result, the hydrogen supply apparatus more surely has a high level of safety.

In a fourth aspect of the present disclosure, there is provided the hydrogen supply apparatus according to the third aspect, in a case where a concentration of hydrogen gas as detected by the hydrogen gas sensor is equal to or higher than the predetermined concentration, the controller either controls the flow control device to stop supply of hydrogen gas to the air path or reduce a flow rate of hydrogen gas that is supplied to the air path or controls the fan to increase a flow rate of the air in the air path. According to the fourth aspect, in a case where a concentration of hydrogen gas as detected by the hydrogen gas sensor is equal to or higher than the predetermined concentration, the flow control device or the fan is controlled as described above. This prevents a gas mixture having a hydrogen gas concentration that is equal to or higher than the predetermined concentration from continuing to be supplied to the interior. As a result, the hydrogen supply apparatus more surely has a high level of safety.

In a fifth aspect of the present disclosure, there is provided the hydrogen supply apparatus according to the third or fourth aspect, in a case where a concentration of hydrogen gas as detected by the hydrogen gas sensor is equal to or higher than the predetermined concentration, the controller controls the fan to increase a flow rate of the air in the air path and then controls the flow control device to stop supply of hydrogen gas to the air path or reduce a flow rate of hydrogen gas that is supplied to the air path. According to the fifth aspect, in a case where a concentration of hydrogen gas as detected by the hydrogen gas sensor is equal to or higher than the predetermined concentration, the flow control device and the fan are controlled as described above. This prevents a gas mixture having a hydrogen gas concentration that is equal to or higher than the predetermined concentration from continuing to be supplied to the interior. As a result, the hydrogen supply apparatus more surely has a high level of safety.

In a sixth aspect of the present disclosure, there is provided the hydrogen supply apparatus according to any one of the third to fifth aspects, further including a temperature sensor disposed between the fan and the inlet in the air path, in a case a temperature detected by the temperature sensor is equal to or higher than a particular temperature, the controller controls the flow control device and the fan to stop supply of hydrogen gas to the air path and stop the fan. According to the sixth aspect, in a case where a temperature detected by the temperature sensor is equal to or higher than the particular temperature, the supply of hydrogen gas is stopped and the fan is stopped. This makes it possible to prevent a gas mixture of high-temperature air and hydrogen gas from being supplied to the interior. As a result, the hydrogen supply apparatus more surely has a high level of safety.

In a seventh aspect of the present disclosure, there is provided the hydrogen supply apparatus according to any one of the first to sixth aspects, the fan may be disposed between the end and the outlet in the air path. According to the seventh aspect, since hydrogen gas supplied to the air path through the first supply port flows through the fan together with air, the hydrogen gas and the air are stirred well, so that the hydrogen gas concentration of air that is blown out from the outlet easily becomes spatially uniform.

In an eighth aspect of the present disclosure, there is provided the hydrogen supply apparatus according to the seventh aspect, the hydrogen gas sensor may be disposed downstream of the fan in a direction of flow the air. According to the eighth aspect, the hydrogen gas sensor detects a concentration of hydrogen gas in a gas mixture of hydrogen gas and air that have been stirred well by the fan, and can therefore appropriately detect a concentration of hydrogen gas.

In a ninth aspect of the present disclosure, there is provided the hydrogen supply apparatus according to any one of the first to sixth aspects, the end may be disposed between the fan and the outlet in the air path. According to the ninth aspect, since hydrogen gas supplied to the air path through the first supply port does not pass through the fan, the hydrogen gas can be prevented from being exposed to static electricity that may be generated by the fan. In addition, since hydrogen gas is supplied to the air path through the first supply port toward a flow of air accelerate by the fan, the hydrogen gas and the air are stirred well, so that the hydrogen gas concentration of a gas mixture that is blown out from the outlet easily becomes spatially uniform.

In a tenth aspect of the present disclosure, there is provided the hydrogen supply apparatus according to any one of the first to ninth aspects, the air path may have a vertically long air path through which to guide the flow of air from a lower position toward a higher position, and the end is disposed in the vertically long air path. Hydrogen gas, which is light, tends to flow upward. According to the tenth aspect, since hydrogen gas is supplied to the vertically long air path through the first supply port, the hydrogen gas is accelerated by an upward flow of air, so that the air and the hydrogen gas are stirred well. For this reason, the hydrogen gas concentration of air that is blown out from the outlet easily becomes spatially uniform.

In an eleventh aspect of the present disclosure, there is provided the hydrogen supply apparatus according to any one of the first to tenth aspects, further including a hydrogen gas supply source that supplies hydrogen gas to the first pipe. According to the eleventh aspect, hydrogen gas can be supplied from the hydrogen gas supply source to the air path through the first supply port.

In a twelfth aspect of the present disclosure, there is provided the hydrogen supply apparatus according to any one of the first to eleventh aspects, the hydrogen gas supply source may include an electrolytic device that produces the hydrogen gas by electrolysis of water. The twelfth aspect makes it possible to produce hydrogen gas by electrolysis of water and supply a mixture of the hydrogen gas and outdoor air to the interior even in an environment provided with no hydrogen gas supply infrastructure. Further, as compared with a case where a pressure tight case having high-pressure hydrogen stored therein is used as a hydrogen gas supply source, there is no need for a task of replacing hydrogen gas supply sources. In addition, since it is only necessary to produce hydrogen by electrolysis of water according to demand for hydrogen supply, it is not necessary to store hydrogen gas for a long period of time.

In a thirteenth aspect of the present disclosure, there is provided the hydrogen supply apparatus according to any one of the first to twelfth aspects, further including a mixer that has a second supply port which is open to the air path, that is supplied with the hydrogen gas from the first pipe, and that dilutes the hydrogen gas with a diluent gas, the hydrogen gas diluted in the mixer may be supplied to the air path through the second supply port. According to the thirteenth aspect, the hydrogen gas diluted in the mixer is supplied to the air path to make contact with air. This makes it possible to more safely supply hydrogen gas to the air path. As a result, the hydrogen supply apparatus has a higher level of safety.

In a fourteenth aspect of the present disclosure, there is provided the hydrogen supply apparatus according to the thirteenth aspect, the mixer may have a flow passage that allows passage of hydrogen gas having passed through the flow control device and a third supply port that is open to the flow passage and that serves to supply the diluent gas to the flow passage. According to the fourteenth aspect, by supplying the diluent gas to the hydrogen gas having passed through the flow control device, the hydrogen gas can be diluted.

In a fifteenth aspect of the present disclosure, there is provided the hydrogen supply apparatus according to the thirteenth or fourteenth aspect, the diluent gas may be a gas that is inert to hydrogen gas. The fifteenth aspect makes it possible to safely dilute hydrogen gas in the mixer.

In a sixteenth aspect of the present disclosure, there is provided the hydrogen supply apparatus according to the fifteenth aspect, the diluent gas may be nitrogen gas. Since nitrogen gas is easily available, the sixteenth aspect makes it possible to achieve a reduction in running costs of the hydrogen supply apparatus.

In a seventeenth aspect of the present disclosure, there is provided the hydrogen supply apparatus according to the sixteenth aspect, further including a gas separator, connected to the mixer, that separates the nitrogen gas from air. According to the seventeenth aspect, the gas separator can separate, from air, nitrogen gas with which to dilute hydrogen gas. This makes it possible to supply nitrogen gas to the mixer even in an environment provided with no hydrogen gas supply infrastructure and makes it possible to achieve a further reduction in running costs of the hydrogen supply apparatus.

In an eighteenth aspect of the present disclosure, there is provided the hydrogen supply apparatus according to any one of the first to seventeenth aspects, further including a filter that is disposed in a first position between the inlet and the fan and between the inlet and the end in the air path, a second position between the outlet and the fan and between the outlet and the end in the air path, or in both the first position and the second position, that is made of an incombustible material, and that both transmits gases and thins out foreign substances. According to the eighteenth aspect, thinning out of foreign substances by the filter makes it possible to prevent the foreign substances from being supplied to the interior. In particular, disposing the filter in the first position makes it possible to prevent static electricity from being generated by contact between foreign substances and the fan. Further, even if fire occurs due to combustion of hydrogen gas in the air path, the spread of fire can be suppressed. In addition, even if fire occurs outside the air path, the spread of the fire to the air path can be prevented. For this reason, the hydrogen supply apparatus has a higher level of safety.

In a nineteenth aspect of the present disclosure, there is provided the hydrogen supply apparatus according to any one of the first to eighteenth aspects, further including a shutter that closes the air path and is disposed in at least one of a third position between the inlet and the fan and between the inlet and the end in the air path, and a fourth position between the outlet and the fan and between the outlet and the end in the air path, or in both the third position and the fourth position and that closes the air path, in a case where a concentration of hydrogen gas as detected by the hydrogen gas sensor is equal to or higher than the predetermined concentration, the controller controls the shutter to close the air path. According to the nineteenth aspect, since the air path is closed by the shutter in a case where a concentration of hydrogen gas as detected by the hydrogen gas sensor is equal to or higher than the predetermined concentration, a gas mixture having a hydrogen gas concentration that is equal to or higher than the predetermined concentration does not continue to be supplied to the interior. For this reason, the hydrogen supply apparatus has a higher level of safety.

In a twentieth aspect of the present disclosure, there is provided the hydrogen supply apparatus according to any one of the first to nineteenth aspects, the air path includes a downstream portion that has a plurality of the outlets. According to the twentieth aspect, a gas mixture obtained by mixing hydrogen gas into air taken into the air path from the exterior can be supplied from the plurality of outlets.

In a twenty-first aspect of the present disclosure, there is provided the hydrogen supply apparatus according to the second aspect, the air path may include a downstream portion that has a plurality of the outlets, and the hydrogen gas sensor is disposed upstream of the downstream portion in a direction of flow of the air. According to the twenty-first aspect, a gas mixture obtained by mixing hydrogen gas into air taken into the air path from the exterior can be supplied from the plurality of outlets. In addition, the concentrations of hydrogen gas in gas mixtures that are supplied from the plurality of outlets, respectively, can be efficiently detected.

In a twenty-second aspect of the present disclosure, there is provided the hydrogen supply apparatus according to any one of the first to twenty-first aspects, the controller may acquire or store first information indicating presence or absence of a human in the interior, and when the first information indicates the presence of a human in the interior, the controller controls the flow control device to supply hydrogen gas to the air path. The twenty-second aspect makes it possible to supply hydrogen gas when a human is present in the interior. This makes it possible to efficiently utilize hydrogen gas.

In a twenty-third aspect of the present disclosure, there is provided the hydrogen supply apparatus according to the twenty-second aspect, the controller may further acquire second information indicating a position of a human in the interior, and controls the flow control device on the basis of the second information to adjust a flow rate of the hydrogen gas. The twenty-third aspect makes it possible to efficiently supply hydrogen gas to a human in the interior according to position.

In a twenty-fourth aspect of the present disclosure, there is provided the hydrogen supply device, the controller may acquire third information that is biological information of a human in the interior, and controls the flow control device on the basis of the third information to adjust a flow rate of the hydrogen gas. The twenty-fourth aspect makes it possible to efficiently supply hydrogen gas according to biological information of a human in the interior.

In a twenty-fifth aspect of the present disclosure, there is provided a hydrogen supply system including: the hydrogen supply apparatus according to any one of the first to twenty-first aspects; and a detector that detects at least either presence or absence of a human in the interior or biological information of a human in the interior. The controller acquires, as the first information, information indicating a result of detection yielded by the detector.

The twenty-fifth aspect brings about the same effect as any one of the first to twenty-first aspects.

In a twenty-sixth aspect of the present disclosure, there is provided the hydrogen supply system according to the twenty-fifth aspect, the detector may further detect information indicating a position of a human in the interior.

An embodiment of the present disclosure is described below with reference to the drawings. It should be noted that the following description pertains to examples of the present disclosure and the present disclosure is not limited to these examples. Arrows in the accompanying drawings conceptually indicate the flow of gases such as air and hydrogen gas. In terms of gas concentration, the symbol "%" herein means the percentage with respect to the volume and typically means the volume ratio at normal atmospheric pressure and 20° C.

As shown in FIG. 1, a hydrogen supply apparatus 1a includes an air path 4, a fan 6, a first pipe 30, and a flow control device 8. The air path 4 has an inlet 3 that is open to an interior and an outlet 2 that is open to an exterior. The fan 6 is disposed in the air path 4 and produces a flow of air from the inlet 3 to the outlet 2. The first pipe 30 has an end 31. The end 31 forms a first supply port 32 through which to supply hydrogen gas to the air path 4. The flow control device 8 is attached to the first pipe 30 and adjusts the flow rate of hydrogen gas that is supplied to the air path 4.

In the hydrogen supply apparatus 1a, the end 31 of the first pipe 30 is disposed, for example, in the air path 4. Alternatively, the end 31 may be disposed outside the air path 4. In this case, an inner part of the first pipe 30 and the air path 4 may be connected to each other via a filter interposed between the inner part of the first pipe 30 and the air path 4.

In the hydrogen supply apparatus 1a, actuation of the fan 6 causes outdoor air to be taken into the air path 4 through the inlet 3 to produce a flow of air from the inlet 3 toward the outlet 2. Hydrogen gas supplied to the air path 4 through the first supply port 32 is mixed with air flowing through the air path 4, and together with outdoor air, the hydrogen gas is supplied to the interior through the outlet 2. The concentration of hydrogen gas in the air path 4 is adjusted by the flow control device 8 to fall within a predetermined range based on a lower explosion limit of hydrogen gas in air. For this reason, the hydrogen supply apparatus 1a is advantageous to assuring a high level of safety.

As shown in FIG. 1, the hydrogen supply apparatus 1a further includes, for example, a hydrogen gas sensor 7. The hydrogen gas sensor 7 is disposed downstream of the end 31 in the direction of flow of air in the air path 4 and detects the concentration of hydrogen gas in the air path 4. The concentration of hydrogen gas in the air path 4 can be detected by the hydrogen gas sensor 7, and a result of the detection can be utilized so that the concentration of hydrogen gas in the air path 4 is adjusted to fall within a predetermined range. For this reason, the hydrogen supply apparatus 1a is advantageous to assuring a high level of safety. The phrase "downstream of the end 31 in the direction of flow of air in the air path 4" means a position between the end 31 and the outlet 2 of the air path 4 or a position downstream of the outlet 2 in the direction of flow of air where the concentration of hydrogen gas in the air path 4 can be detected.

The fan 6 is disposed in a position closer to the outlet 2 than to the inlet 3 in a direction of an axis of the air path 4. Actuation of the fan 6 causes negative pressure upstream of the fan 6 in the direction of flow of air. For this reason, as long as the fan 6 is disposed in a position closer to the outlet 2 than to the inlet 3 in the direction of the axis of the air path 4, air can be prevented from flowing out through a gap between constituent components that define the air path 4 over a wide range in the air path 4 and staying in the hydrogen supply apparatus 1a or another space. As a result, the hydrogen supply apparatus 1a has a high level of safety.

As shown in FIG. 1, the hydrogen supply apparatus 1a further includes, for example, a hydrogen gas supply source 9. Hydrogen gas is supplied from the hydrogen gas supply source 9 to the first pipe 30. Although, in FIG. 1, the hydrogen gas supply source 9 is connected to the first pipe 30 via the flow control device 8, this is not intended to impose any limitation. For example, the hydrogen gas supply source 9 and the first pipe 30 may be connected to each other via a member, such as a filter, interposed between the hydrogen gas supply source 9 and the first pipe 30. Further, the first pipe 30 may be directly connected to the hydrogen gas supply source 9. Examples of the hydrogen gas supply source 9 include, but are not particularly limited to, a pressure tight case containing high-pressure hydrogen. The hydrogen gas supply source 9 may be one that includes an electrolytic device which produces hydrogen gas by electrolysis of water. The hydrogen gas supply source 9 may be a hydrogen gas supply source for supplying hydrogen to a fuel cell power facility. The hydrogen gas supply source 9 may contain, in addition to hydrogen, a component that is inert to hydrogen.

Hydrogen gas may be supplied to the air path 4 with the first pipe 30 connected to a gas valve through which to supply hydrogen gas. In this case, the hydrogen supply apparatus 1a does not necessarily need to include the hydrogen gas supply source 9.

The flow control device 8 typically adjusts the mass flow rate of hydrogen gas. The flow control device 8 is constituted, for example, by a mass flow controller. The mass flow controller includes a sensor, a control circuit, and a valve. In the mass flow controller, a signal representing a mass flow rate of hydrogen gas as detected by the sensor is inputted to the control circuit, and on the basis of the input, the control circuit generates a control signal to control the valve. When the flow control device 8 is constituted by a mass flow controller, the mass flow rate of hydrogen gas can be more accurately adjusted than in a case where the flow rate of hydrogen gas is controlled solely by a valve. The flow control device 8 may for example be a combination of a flow rate sensor and a flow control valve or may be a flow control valve alone. The flow control device 8 thus configured is inexpensive, which leads to a reduction in manufacturing cost of the hydrogen supply apparatus 1a.

The hydrogen gas sensor 7 is for example a publicly-known gas sensor such as a resistance gas sensor, a solid state gas sensor, or an electrothermal gas sensor. It is desirable that the hydrogen gas sensor 7 have high sensitivity in a particular range of hydrogen gas concentrations (e.g. 1 to 5% or lower). The hydrogen gas sensor 7 is typically an electrothermal gas sensor. Using an electrothermal gas sensor as the hydrogen gas sensor 7 makes it possible to precisely detect the concentration of hydrogen gas in air in a range of hydrogen gas concentrations of approximately 0.5 ppm (parts per million) to approximately 5%.

The end 31 is disposed in the center of the air path 4, which is on or near the axis of the air path 4. Since air flows at a high velocity in the center of the air path 4, disposing the end 31 in the center of the air path 4 causes hydrogen gas to be supplied toward the flow of air flowing at a high velocity, so that the hydrogen gas and the air are stirred well. The first supply port 32 has, for example, an upward opening. This makes it easy for hydrogen gas to be diffused in the air path 4, so that the hydrogen gas and air are stirred well.

As shown in FIG. 1, the hydrogen supply apparatus 1a further includes a controller 10. The controller 10 controls the flow control device 8 so to keep the concentration of hydrogen gas at the outlet 2 lower than a predetermined concentration (e.g. 4%). The predetermined concentration is set to be equal to or lower than the lower explosion limit of hydrogen gas in air. The flow control device 8 and the controller 10 are connected to each other by cable or by radio so that they can exchange signals such as detection signals and control signals with each other. The flow control device 8 has, for example, a function of detecting the mass flow rate of hydrogen gas, and a signal representing a mass flow rate of hydrogen gas as detected by the flow control device 8 is inputted to the controller 10. Further, the controller 10 sends a control signal to the flow control device 8, and the flow control device 8 operates in accordance with the control signal.

The controller 10 is for example a computer including an interface, an arithmetic device such as a CPU, and a storage device such as a RAM or a ROM. The controller 10 has stored therein a program needed for operation of the hydrogen supply apparatus 1a.

The fan 6 is connected to the controller 10 by cable or by radio so as to be able to receive a control signal that is transmitted from the controller 10. As shown in FIG. 1, the hydrogen supply apparatus 1a further includes, for example, an air volume sensor 13. The air volume sensor 13 is disposed, for example, between the fan 6 and the inlet 3 in the air path 4. The air volume sensor 13 is for example a thermal air volume sensor. The controller 10 is for example connected to the air volume sensor 13 by cable or by radio so as to be able to receive, from the air volume sensor 13, a signal representing a result of detection yielded by the air volume sensor 13.

For example, in a case where a concentration of hydrogen gas as detected by the hydrogen gas sensor 7 is equal to or higher than the predetermined concentration, the controller 10 controls the flow control device 8 to stop the supply of hydrogen gas to the air path 4 or reduce the flow rate of hydrogen gas that is supplied to the air path 4. Alternatively, the controller 10 controls the fan 6 to increase the flow rate of air in the air path 4. This prevents a gas mixture having a hydrogen gas concentration that is equal to or higher than the predetermined concentration from continuing to be supplied to the interior. For this reason, the hydrogen supply apparatus 1a more surely has a high level of safety.

For example, in a case where a concentration of hydrogen gas as detected by the hydrogen gas sensor 7 is equal to or higher than the predetermined concentration, the controller 10 controls the fan 6 to increase the flow rate of air in the air path 4. After that, the controller 10 for example controls the flow control device 8 to stop the supply of hydrogen gas to the air path 4 or reduce the flow rate of hydrogen gas that is supplied to the air path 4. In this case, a gas mixture having a hydrogen gas concentration that is equal to or higher than the predetermined concentration does not continue to be supplied to the interior, so that the hydrogen supply apparatus 1a more surely has a high level of safety.

For example, after having controlled the flow control device 8 to stop the supply of hydrogen gas tot the air path 4, the controller 10 controls the fan 6 to stop the fan 6. In other words, the controller 10 lets the fan 6 operate during a period in which hydrogen gas is being supplied to the air path 4. This makes it possible to prevent hydrogen gas from being supplied to the air path 4 with no flow of air produced therein.

The controller 10 further includes, for example, a temperature sensor 13a. The temperature sensor 13a is disposed between the fan 6 and the inlet 3 in the air path 4. For example, in a case where a temperature detected by the temperature sensor 13a is equal to or higher than a particular temperature (e.g. 40° C.), the controller 10 controls the flow control device 8 and the fan 6 to stop the supply of hydrogen gas to the air path 4 and stop the fan 6. In this case, the supply of a gas mixture of high-temperature air and hydrogen gas to the interior can be prevented, so that the hydrogen supply apparatus 1a more surely has a high level of safety. The controller 10 is for example connected to the temperature sensor 13a by cable or by radio so as to be able to receive a signal representing a result of detection yielded by the temperature sensor 13a.

The temperature sensor 13a is incorporated, for example, in the air volume sensor 13. In this case, the temperature sensor 13a can be utilized for control of the flow control device 8 and the fan 6 as well as for temperature compensating of a result of detection yielded by the air volume sensor 13. The temperature sensor 13a may be disposed independently of the air volume sensor 13.

As shown in FIG. 1, the fan 6 is disposed between the end 31 and the outlet 2, for example, in the air path 4. The fan 6 is disposed, for example, downstream of the end 31 in the direction of flow of air. Since hydrogen gas supplied to the air path 4 through the first supply port 32 flows through the fan 6 together with air, the hydrogen gas and the air are stirred well, so that the hydrogen gas concentration of air that is blown out from the outlet 2 easily becomes spatially uniform.

In a case where the fan 6 is disposed between the end 31 and the outlet 2 in the air path 4, the hydrogen gas sensor 7 is disposed, for example, downstream of the fan 6 in the direction of flow of air. As a result, the hydrogen gas sensor 7 detects a concentration of hydrogen gas in a gas mixture of hydrogen gas and air that have been stirred well by the fan 6, and can therefore appropriately detect a concentration of hydrogen gas. The phrase "downstream of the fan 6 in the direction of flow of air" means a position between the outlet 2 of the air path 4 and the fan 6 or a position downstream of the outlet 2 in the direction of flow of air where the concentration of hydrogen gas in the air path 4 can be detected.

As shown in FIG. 1, the air path 4 has, for example, a vertically long air path 4a through which to guide the flow of air from a lower position toward a higher position. The end 31 is disposed, for example, in the vertically long air path 4a. Hydrogen gas, which is light, tends to flow upward. In this case, since hydrogen gas is supplied to the vertically long air path 4a through the first supply port 32, the hydrogen gas is accelerated by an upward flow of air, so that the air and the hydrogen gas are stirred well. For this reason, the hydrogen gas concentration of air that is blown out from the outlet 2 easily becomes spatially uniform.

The hydrogen gas sensor 7 is disposed, for example, at or near an upper end of the vertically long air path 4a. In this case, a concentration of hydrogen gas can be appropriately detected, as a concentration of hydrogen gas in a gas mixture of hydrogen gas and air that have been stirred well by an upward flow of air is detected.

As shown in FIG. 1, the hydrogen supply apparatus 1a further includes, for example, a mixer 20. The mixer 20 has a second supply port 5 that is open to the air path 4. In addition, hydrogen gas is supplied to the mixer 20 from the first pipe 30. The mixer 20 dilutes hydrogen gas with a diluent gas. The mixer 20 is typically disposed between the flow control device 8 and the second supply port 5. In this case, hydrogen gas diluted in the mixer 20 is supplied to the air path 4 through the second supply port 5. For this reason, the hydrogen gas diluted in the mixer 20 is supplied to the air path 4 to make contact with air. This prevents hydrogen from making contact with oxygen without having been diluted, thus making it possible to more safely supply hydrogen gas to the air path 4 without explosion or combustion of hydrogen. As a result, the hydrogen supply apparatus 1a has a higher level of safety.

The mixer 20 has, for example, a flow passage 21 and a third supply port 22. The flow passage 21 allows passage of hydrogen gas having passed through the flow control device 8. The flow passage 21 is present, for example, inside a cylinder. The third supply port 22 is open to the flow passage 21 and serves to supply the diluent gas to the flow passage 21. In this case, by supplying the diluent gas to the hydrogen gas having passed through the flow control device 8, the hydrogen gas can be diluted.

The diluent gas with which hydrogen gas is diluted in the mixer 20 is typically a gas that is inert to hydrogen gas. This makes it possible to safely dilute hydrogen gas.

The diluent gas is for example nitrogen gas. In this case, since nitrogen gas is easily available, a reduction in running costs of the hydrogen supply apparatus 1a can be achieved.

The hydrogen supply apparatus 1a further includes, for example, a second flow control device 22a. The second flow control device 22a adjusts the flow rate of a diluent gas that is supplied to the mixer 20. The second flow control device 22a typically adjusts the mass flow rate of a diluent gas and is constituted, for example, by a mass flow controller. The second flow control device 22a and the controller 10 are connected to each other by cable or by radio so as to be able to exchange signals such as detection signals and control signals with each other. The second flow control device 22a has, for example, a function of detecting the mass flow rate of a diluent gas, and a signal representing a mass flow rate of a diluent gas as detected by the second flow control device 22a is inputted to the controller 10. Further, the controller 10 sends a control signal to the second flow control device 22a, and the second flow control device 22a operates in accordance with the control signal.

The hydrogen supply apparatus 1a further includes, for example, a fourth supply port 12 and a third flow control device 12a. The fourth supply port 12 serves to supply oxygen gas to the air path 4. The third flow control device 12a adjusts the flow rate of oxygen gas that is supplied to the air path 4. The third flow control device 12a typically serves to adjust the mass flow rate of oxygen gas and is constituted, for example, by a mass flow controller. The third flow control device 12a and the controller 10 are connected to each other by cable or by radio so as to be able to exchange signals such as detection signals and control signals with each other. The third flow control device 12a has, for example, a function of detecting the mass flow rate of oxygen gas, and a signal representing a mass flow rate of oxygen gas as detected by the third flow control device 12a is inputted to the controller 10. Further, the controller 10 sends a control signal to the third flow control device 12a, and the third flow control device 12a operates in accordance with the control signal. The fourth supply port 12 is disposed, for example, downstream of the second supply port 5 in the direction of flow of air.

As show in FIG. 1, the hydrogen supply apparatus 1a includes, for example, a filter 2a and a filter 3a. The filter 3a is disposed in a first position. The first position is a position between the inlet 3 and the fan 6 and between the inlet 3 and the end 31 in the air path 4. The filter 2a is disposed in a second position. The second position is a position between the outlet 2 and the fan 6 and between the outlet 2 and the end 31 in the air path 4. Instead of including filters disposed in both the first position and the second position, respectively, the hydrogen supply apparatus 1a may include a filter disposed in either the first position or the second position.

The filter 2a and the filter 3a are each made of an incombustible material and both transmit gases and captures foreign substances.

Thinning out of foreign substances by the filter 2a or the filter 3a makes it possible to prevent the foreign substances from being supplied to the interior. In particular, by including the filter 3a, the hydrogen supply apparatus 1a can prevent static electricity from being generated by contact between foreign substances and the fan 6. Further, even if fire occurs due to combustion of hydrogen gas in the air path 4, the spread of fire can be suppressed. In addition, even if fire occurs outside the air path 4, the spread of the fire to the air path 4 can be prevented. For this reason, the hydrogen supply apparatus 1a has a higher level of safety. Furthermore, by including the filter 2a and the filter 3a, the hydrogen supply apparatus 1a makes it hard for the flow of air in the air path 4 to be affected by the flow of air outside the air path 4, thus stabilizing the flow of air in the air path 4. In a case where the hydrogen supply apparatus 1a includes both the filter 2a and the filter 3a, the filter 2a and the filter 3a may be made of materials that are different from each other. The filter 3a is disposed in a position closer to the inlet 3 than the filter 2a and is therefore more susceptible to outdoor conditions such as rain or wind than the filter 2a. For this reason, the filter 3a is for example a high-strength metallic net. On the other hand, the filter 2a is for example a woven fabric of non-flammable fibers in consideration of indoor fire and foreign substances.

The filter 2a and the filter 3a are each for example a net of metal or a net, woven fabric, or unwoven fabric of non-flammable fibers. The filter 2a and the filter 3a each comply with Incombustibility Grade 1 under Japanese Industrial Standards (JIS) A 1321-1994.

Figure 2:
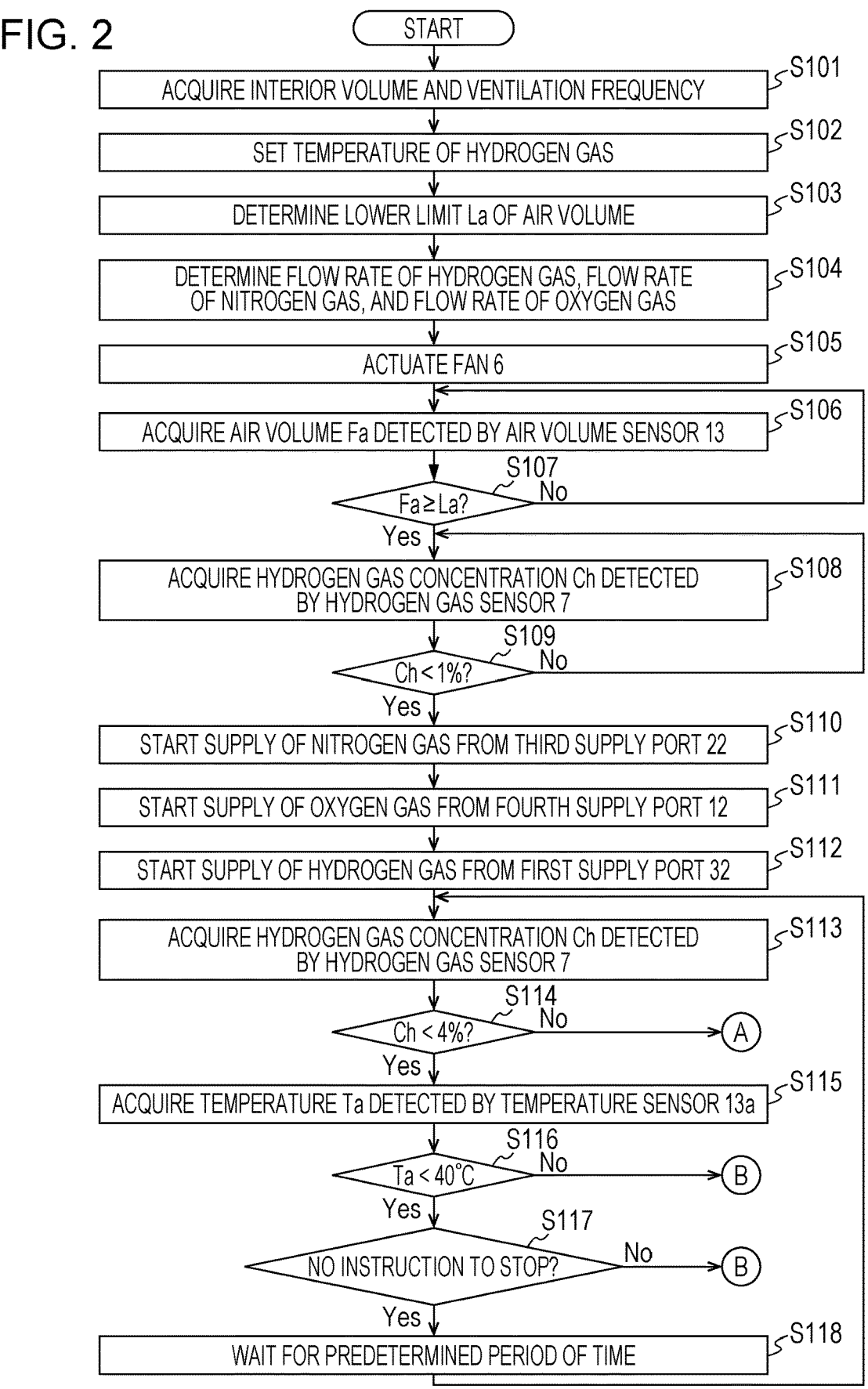
FIG. 2 is a flow chart showing an example of operation of the hydrogen supply apparatus of FIG. 1.

Next, an example of operation of the hydrogen supply apparatus 1a is described. As shown in FIG. 2, upon an instruction to start operation of the hydrogen supply apparatus 1a, in step S101, the controller 10 acquires an interior volume [m$^3$] and a ventilation frequency [times/hour]. The interior volume is set, for example, in default configuration of the hydrogen supply apparatus 1a. The ventilation frequency may be set in default configuration of the hydrogen supply apparatus 1a or may be set on the basis of an user's input to a control panel (not illustrated) that is capable of communicating with the controller 10 at the start of operation of the hydrogen supply apparatus 1a. The ventilation frequency may be changed during operation of the hydrogen supply apparatus 1a. In this case, in order to quickly increase the concentration of hydrogen gas in the interior, it is desirable that a ventilation frequency during a predetermined period of time from the start of operation of the hydrogen supply apparatus 1a be set to be higher than a ventilation frequency after passage of the predetermined period of time. Next, the controller 10 proceeds to step S102 to set the concentration [%] of hydrogen gas in air that is supplied to the interior. For example, the concentration of hydrogen gas is set to a particular value of lower than 4%. Next, the controller 10 proceeds to step S103 to determine a lower limit La of air volume, which is the flow rate of air that is supplied from the exterior to the air path 4. The lower limit La of air volume is determined, for example, by the interior volume, the ventilation frequency, and a mixing ratio between air in the air path 4 supplied from the exterior and other gasses such as hydrogen gas. For example, in a case where the interior volume is 32 [m$^3$], the ventilation frequency is 0.5 (times/hour), and the mixing ratio on a volumetric basis between air in the air path 4 supplied from the exterior and other gasses such as hydrogen gas is 9:1, the lower limit La of air volume is 14.4 [m$^3$/hour] (=32 [m$^3$]×0.5 [times/hour]×0.9). Next, the controller 10 proceeds to step S104 to determine the flow rate of hydrogen gas that is supplied to the air path 4, the flow rate of nitrogen gas in the air path 4, and the flow rate of oxygen gas in the air path 4. The flow rate of hydrogen gas that is supplied to the air path 4 is determined, for example, on the basis of the interior volume, the ventilation frequency, and a set value of the concentration of hydrogen gas. For example, in a case where the interior volume and the ventilation frequency are as noted above and the set value of the concentration of hydrogen gas is 3%, the flow rate of hydrogen gas that is supplied to the air path 4 is determined as 0.48 [m$^3$/hour] (=32 [m$^3$]×0.5 [times/hour]×0.03). In this case, for example, the flow rate of nitrogen gas that is supplied from the outlet 2 is determined as 12.32 [m$^3$/hour] (=32 [m$^3$]×0.5 [times/hour]×0.77), and the flow rate of oxygen gas that is supplied from the outlet 2 is determined as 3.20 [m$^3$/hour] (=32 [m$^3$]×0.5 [times/hour]×0.20).

Next, the controller 10 proceeds to step S105 to actuate the fan 6. In this case, the controller 10 determines the number of revolutions of the fan 6 on the basis of the lower limit La of air volume and transmits a control signal to the fan 6 on the basis of a result of the determination. The controller 10 determines the number of revolutions of the fan 6, for example, so that the flow rate of air that is supplied from the exterior to the air path 4 is equal to or higher than the lower limit La of air volume. Next, the controller 10 proceeds to step S106 to acquire information indicating an air volume Fa detected by the air volume sensor 13. Next, the controller 10 proceeds to step S107 to determine whether the air volume Fa detected by the air volume sensor 13 is equal to or higher than the lower limit La of air volume. In a case where a result of the determination in step S107 is negative, the controller 10 returns to step S106. At this point of time, the controller 10 may execute step S106 after having increased the number of revolutions of the fan 6 as needed. In a case where the result of the determination in step S107 is positive, the controller 10 proceeds to step S108 to acquire information indicating a hydrogen gas concentration Ch detected by the hydrogen gas sensor 7. Next, the controller 10 proceeds to step S109 to determine whether the hydrogen gas concentration Ch is lower than a predetermined concentration (e.g. 1%). If air supplied from the exterior is mixed with hydrogen gas for some reason, a result of the determination in step S109 may be a negative result. In a case where the result of the determination in step S109 is negative, it is not appropriate to start to the supply of hydrogen gas; therefore the controller 10 returns to step S108 to repeat steps S108 and S109 until the hydrogen gas concentration Ch becomes lower than 1%.

In a case where the result of the determination in step S109 is positive, the controller 10 proceeds to step S110 to start the supply of nitrogen gas from the third supply port 22. In this case, the controller 10 controls the second flow control device 22a so that the flow rate of nitrogen gas in the air path 4 takes on the value determined in step S104. Specifically, the controller 10 sends, to the second flow control device 22a, a control signal for causing the flow rate of nitrogen gas in the air path 4 to take on the value determined in step S104, and the second flow control device 22a operates in accordance with the control signal. Next, the controller 10 proceeds to step S111 to start the supply of oxygen gas from the fourth supply port 12. In this case, the controller 10 controls the third flow control device 12a so that the flow rate of oxygen gas in the air path 4 takes on the value determined in step S104. Specifically, the controller 10 sends, to the third flow control device 12a, a control signal for causing the flow rate of oxygen gas in the air path 4 to take on the value determined in step S104, and the third flow control device 12a operates in accordance with the control signal. Next, the controller 10 proceeds to step S112 to start the supply of hydrogen gas from the first supply port 32. In this case, the controller 10 controls the flow control device 8 so that the flow rate of hydrogen gas that is supplied to the air path 4 takes on the value determined in step S104. Specifically, the controller 10 sends, to the flow control device 8, a control signal for causing the flow rate of hydrogen gas that is supplied to the air path 4 to take on the value determined in step S104, and the flow control device 8 operates in accordance with the control signal.

Assume a case where the mixing ratio on a volumetric basis between air $A_{OUT}$ that is supplied from the exterior to the air path 4 and a combination of hydrogen gas $M_{HN}$, diluted with nitrogen gas, that is supplied from the second supply port 5 and oxygen gas $O_{SUP}$ that is supplied from the fourth supply port 12 is 9:1. In this case, for example, the volume percentages of oxygen gas, hydrogen gas, and nitrogen gas in the air $A_{OUT}$, the combination of the diluted hydrogen gas $M_{HN}$ and the oxygen gas $O_{SUP}$, and the gas mixture are as shown in Table 1. Although Table 1 describes the concentration ($O_{SUP}$) of oxygen gas as 20%, the gas mixture may be prepared by adjusting the concentrations of hydrogen gas and nitrogen gas while making the concentration of oxygen gas 0%.

TABLE 1

| | Air $A_{OUT}$ | Diluted hydrogen gas $M_{HN}$ and oxygen gas $O_{SUP}$ | Gas mixture |
|---|---|---|---|
| Oxygen gas [%] | 20 | 20 | 20 |
| Hydrogen gas [%] | NA | 30 | 3 |
| Nitrogen gas [%] | 80 | 50 | 77 |

Ideally, it would be nice if the hydrogen supply apparatus 1a can be operated as noted in Table 1; however, in reality, factors conspire to raise the possibility of fluctuations in concentration of hydrogen gas in the gas mixture. For this reason, it is desirable that step S113 and subsequent steps be further executed.

In step S113, the controller 10 acquires information indicating the hydrogen gas concentration Ch detected by the hydrogen gas sensor 7. Next, the controller 10 proceeds to step S114 to determine whether the hydrogen gas concentration Ch is lower than 4%. In a case where a result of the determination in step S114 is positive, the controller 10 proceeds to step S115 to acquire a temperature Ta detected by the temperature sensor 13a. Next, the controller 10 proceeds to step S116 to determine whether the temperature Ta is lower than 40° C. In a case where a result of the determination in step S116 is positive, the controller 10 proceeds to step S117 to determine the presence or absence of an instruction to stop the hydrogen supply apparatus 1a. In a case where, in step S117, there is no instruction to stop the hydrogen supply apparatus 1a, the controller 10 proceeds to step S118 to wait for a predetermined period of time and returns to step S113.

Figure 3:
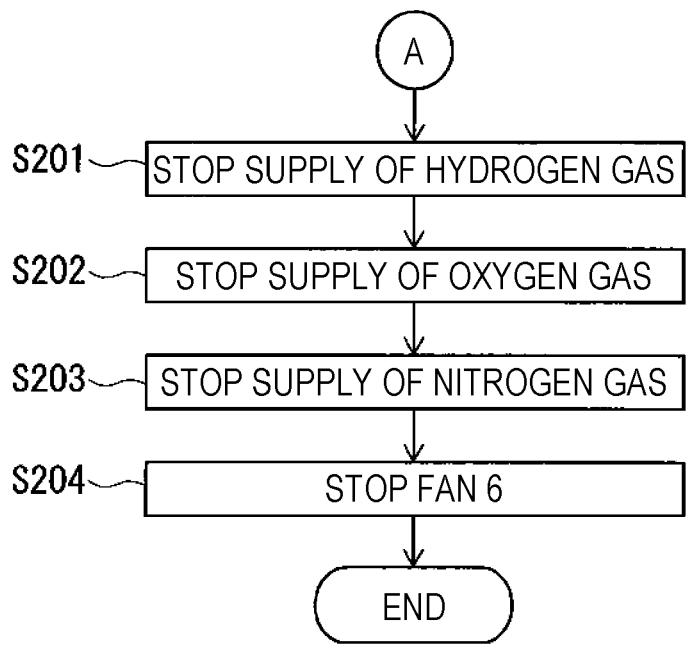
FIG. 3 is a flow chart showing an example of operation of the hydrogen supply apparatus of FIG. 1, together with FIG. 2.

In a case where the result of the determination in step S114 is negative, the controller 10 proceeds to step S201, shown in FIG. 3, to control the flow control device 8 to stop the supply of hydrogen gas. Next, the controller 10 proceeds to step S202 to control the third flow control device 12a to stop the supply of oxygen gas from the fourth supply port 12. Next, the controller 10 proceeds to step S203 to control the second flow control device 22a to stop the supply of nitrogen gas from the third supply port 22. Next, the controller 10 proceeds to step S204 to control the fan 6 to stop the fan 6. Thus, the series of steps ends.

Figure 4:
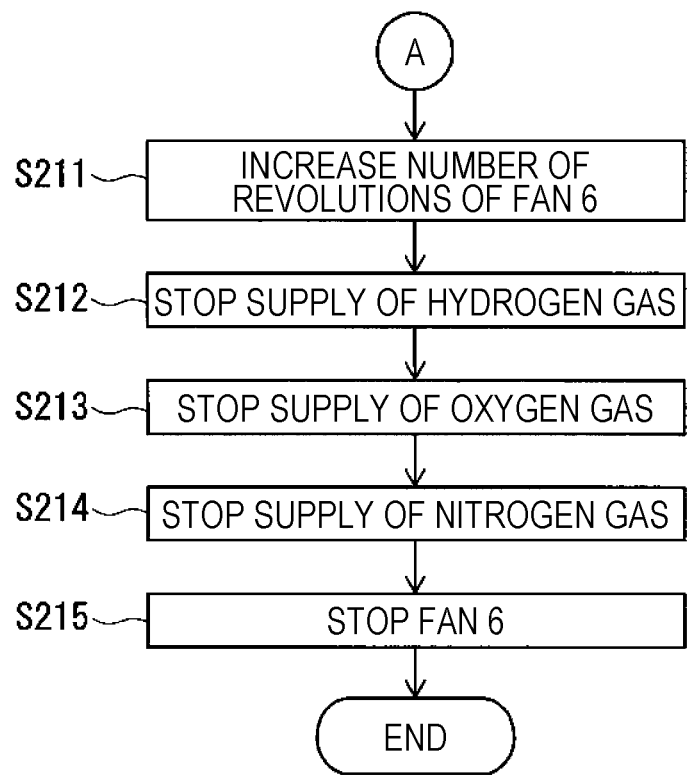
FIG. 4 is a flow chart showing another example of operation of the hydrogen supply apparatus of FIG. 1.

In a case where the result of the determination in step S114 is negative, the controller 10 may proceed to step S211 shown in FIG. 4. In this case, in step S211, the controller 10 controls the fan 6 to increase the flow rate of air in the air path 4. Specifically, the controller 10 increases the number of revolutions of the fan 6. After that, steps S212, S213, S214, and S215 are executed in a similar manner to steps S201, S202, S203, and S204, respectively.

Figure 5:
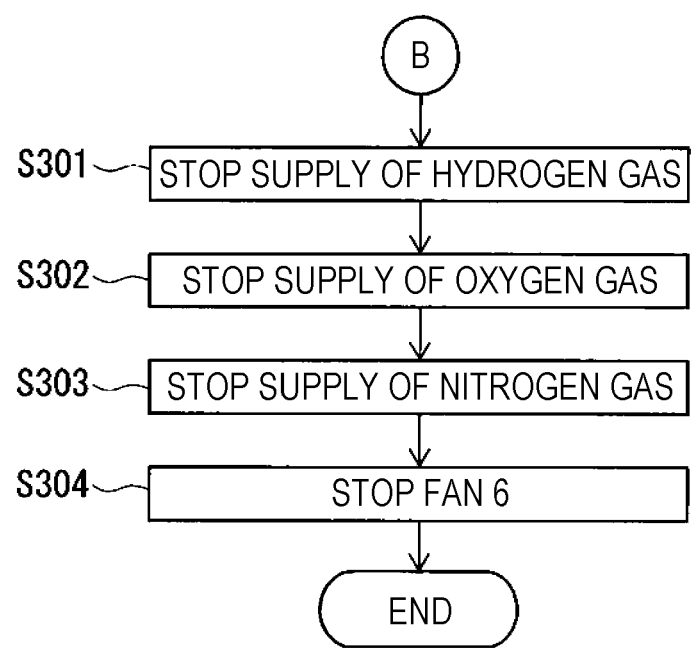
FIG. 5 is a flow chart showing an example of operation of the hydrogen supply apparatus of FIG. 1, together with FIG. 2.

In a case where the result of the determination in step S116 is negative or a case where, in step S117, there is an instruction to stop the hydrogen supply apparatus 1a, steps S301 to S304 shown in FIG. 5 are executed. Steps S301, S302, S303, and S304 are executed in a similar manner to steps S201, S202, S203, and S204, respectively. Thus, the series of steps ends.

Figure 6:
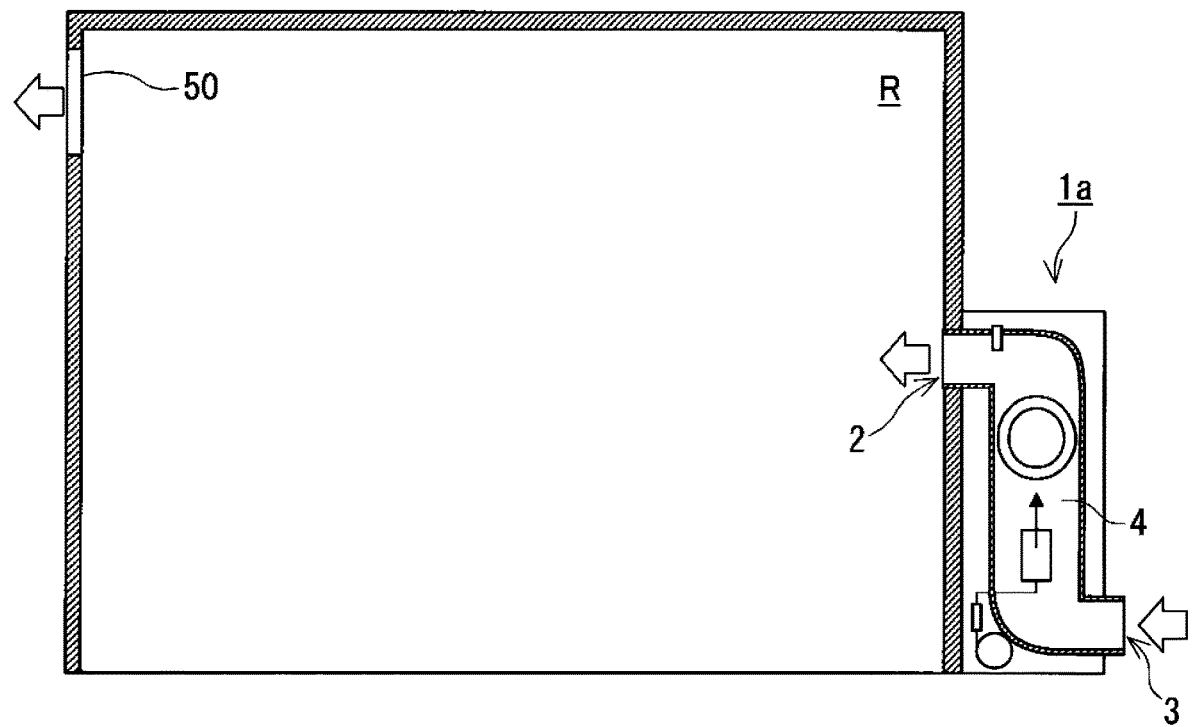
FIG. 6 is a diagram showing an example of a state of installation of the hydrogen supply apparatus of FIG. 1.

For example, as shown in FIG. 6, the hydrogen supply apparatus 1a is installed so that a part of the air path 4 that surrounds the outlet 2 is located inside a through hole formed in a wall partitioning a room R from the exterior. The room R typically has an exhaust port 50. Hydrogen gas is mixed with outdoor air and supplied to the room R by the hydrogen supply apparatus 1a. This causes the room R to be filled with a gas mixture of fresh outdoor air and hydrogen gas. Further, in the gas mixture supplied by the hydrogen supply apparatus 1a, the existing air in the room R is exhausted to the exterior through the exhaust port 50. This ventilation scheme falls under the category of second-class ventilation schemes. It is desirable that the outlet 2 and the exhaust port 50 be located along a pair of wall surfaces that are most distant from each other in a plan view of the room R. Further, it is desirable that the distance between the outlet 2 and the exhaust port 50 in a height direction of the room R be equal to or greater than ½ of the distance between the ceiling and the floor of the room R. In this case, a gas mixture of air and hydrogen gas is easily spread evenly all parts of the room R. The exhaust port 50 may be provided with an exhaust fan. In this case, a ventilation scheme involving the use of the hydrogen supply apparatus 1a falls under the category of first-class ventilation schemes.

The hydrogen supply apparatus 1a is not only installed so as to be able to supply a gas mixture of outdoor air and hydrogen gas to a normal interior such as a room of a house but also may be installed so as to be able to supply a gas mixture to a comparatively small room, such as a hyperbaric chamber, that can accommodate only one person.

Modifications

The hydrogen supply apparatus 1a is can be modified from various points of view. For example, the mixer 20 may be omitted so that hydrogen gas may be supplied to the air path 4 through the first supply port 32 without being diluted. Further, the fourth supply port 12 through which to supply oxygen gas to the air path 4 may also be omitted. The hydrogen supply apparatus 1a may be modified to further include, for example, an infrared sensor. The infrared sensor observes the interior with which the outlet 2 is in contact. The infrared sensor is connected to the controller 10 by radio or by cable so that the controller 10 can receive information indicating a result of observation yielded by the infrared sensor. When the infrared sensor has observed the presence of a spot of a particular temperature (e.g. 80° C.) of higher in the interior, the controller 10 controls the flow control device 8 to stop the supply of hydrogen gas, and stops the fan 6. This process is executed, for example, as an interrupt process during a period of operation of the hydrogen supply apparatus 1a. This prevents a gas mixture of hydrogen gas and outdoor air from being supplied to the interior when a spot of a particular temperature or higher is present in the interior.

The hydrogen supply apparatus 1a may be modified to have a structure in which the outlet 2 is suitable to being disposed in the ceiling of the room R. In this case, the air path 4 does not need to have the vertically long air path 4a.

The hydrogen supply apparatus 1a may be modified such that the fan 6 is disposed in a position closer to the inlet 3 than to the outlet 2 in the direction of the axis of the air path 4. Actuation of the fan 6 causes positive pressure downstream of the fan 6 in the direction of flow of air. For this reason, as long as the fan 6 is disposed in a position closer to the inlet 3 than to the outlet 2 in the direction of the axis of the air path 4, outside air hardly flows in through a gap between constituent components that define the air path 4 over a wide range in the air path 4. This makes it hard for foreign substances to enter the air path 4 and makes it possible to enhance the safety of the hydrogen supply apparatus 1a.

Figure 7:
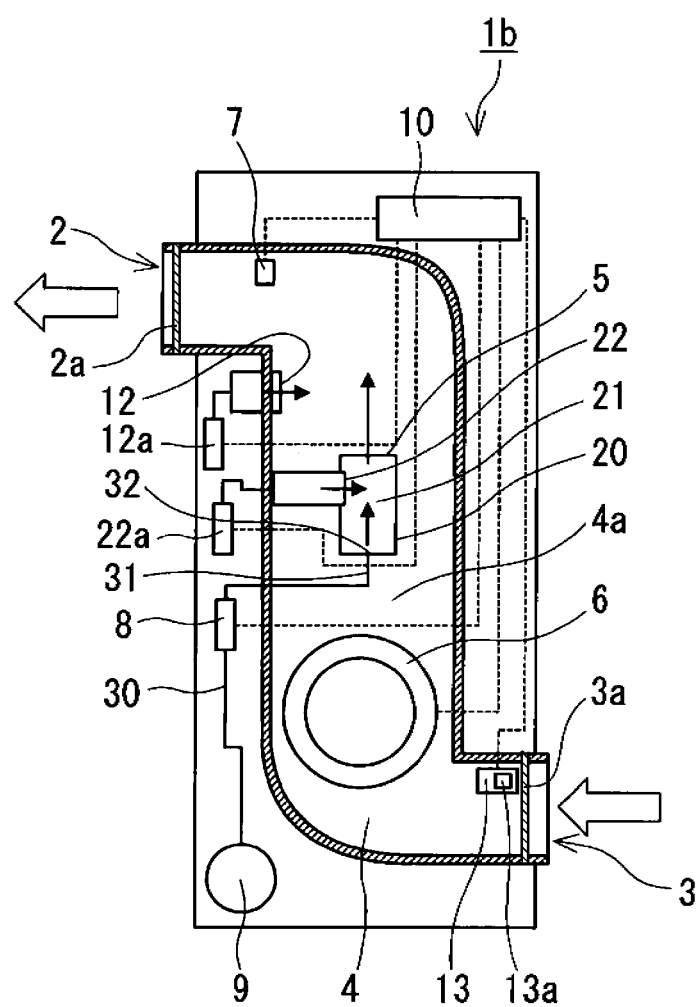
FIG. 7 is a diagram showing another example of a hydrogen supply apparatus of the present disclosure.
Figure 8:
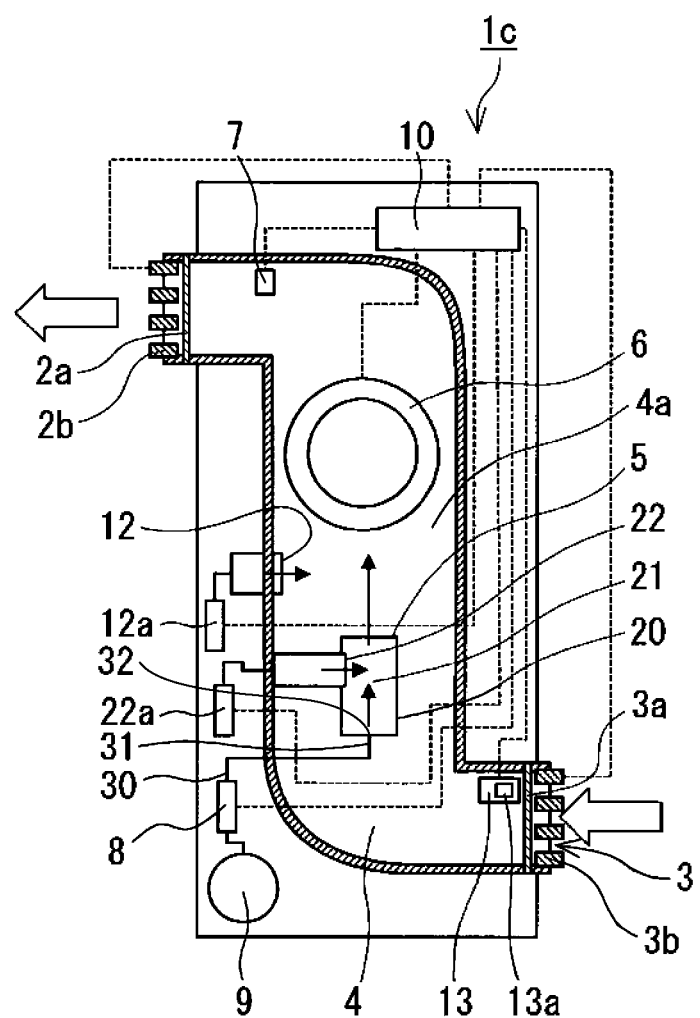
FIG. 8 is a diagram showing still another example of a hydrogen supply apparatus of the present disclosure.
Figure 10:
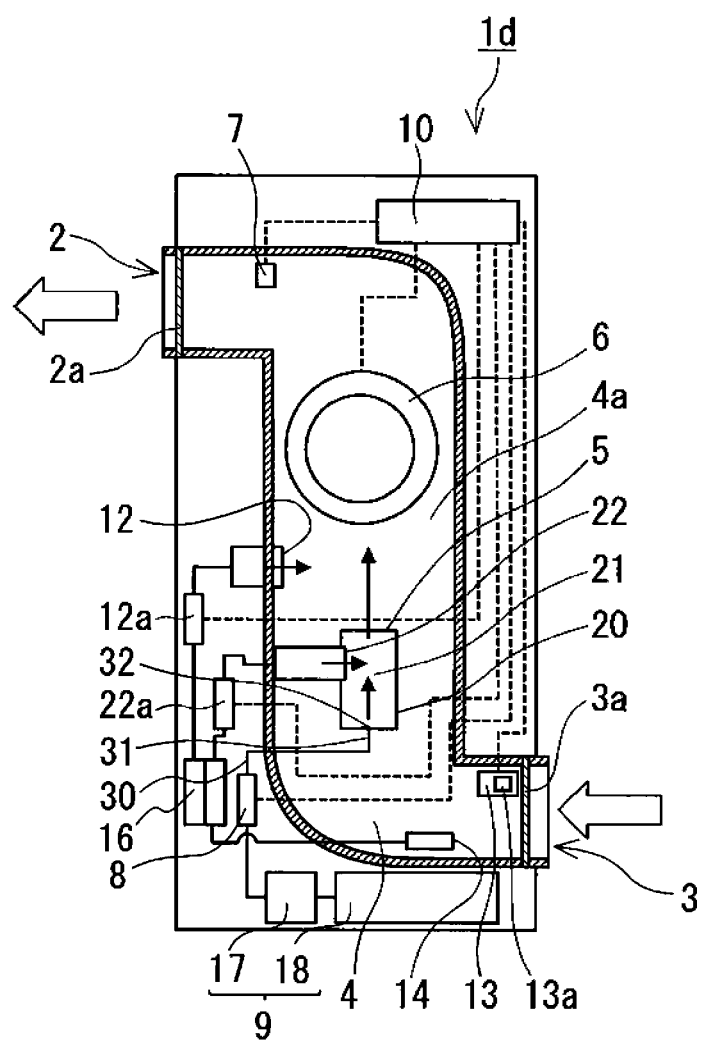
FIG. 10 is a diagram showing still another example of a hydrogen supply apparatus of the present disclosure.

The hydrogen supply apparatus 1a may be modified to be like hydrogen supply apparatuses 1b, 1c, and 1d shown in FIGS. 7, 8, and 10, respectively. The hydrogen supply apparatuses 1b, 1c, and 1d are configured in the same manner as the hydrogen supply apparatus 1a unless otherwise noted. Constituent elements of the hydrogen supply apparatuses 1b, 1c, and 1d which are identical to or correspond to those of the hydrogen supply apparatus 1a are given the same reference signs and are not described in detail below. The foregoing description of the hydrogen supply apparatus 1a applies to the hydrogen supply apparatuses 1b, 1c, and 1d unless a technical contradiction arises.

As shown in FIG. 7, the hydrogen supply apparatus 1b is configured such that the end 31 is disposed between the fan 6 and the outlet 2 of the air path 4 in the air path 4. The end 31 is disposed downstream of the fan 6 in the direction of flow of air. In this case, since hydrogen gas supplied to the air path 4 through the first supply port 32 does not pass through the fan 6, the hydrogen gas can be prevented from being exposed to static electricity that may be generated by the fan 6. In addition, since hydrogen gas is supplied to the air path 4 through the first supply port 32 toward a flow of air accelerate by the fan 6, the hydrogen gas and the air are stirred well, so that the hydrogen gas concentration of a gas mixture that is blown out from the outlet 2 easily becomes spatially uniform.

As shown in FIG. 8, the hydrogen supply apparatus 1c includes a shutter 2b and a shutter 3b. The shutter 3b is disposed in a third position. The third position is a position between the inlet 3 and the fan 6 and between the inlet 3 and the end 31 in the air path 4. The shutter 2b is disposed in a fourth position. The fourth position is a position between the outlet 2 and the fan 6 and between the outlet 2 and the end 31 in the air path 4. Instead of including shutters disposed in both the third position and the fourth position, respectively, the hydrogen supply apparatus 1c may include a shutter disposed in either the third position or the fourth position. The shutter 2b and the shutter 3b each close the air path 4. In a case where a concentration of hydrogen gas as detected by the hydrogen gas sensor 7 is equal to or higher than the predetermined concentration, the controller 10 controls the shutter 2b and the shutter 3b to close the air path 4. The shutter 2b and the shutter 3b each include, for example, a plurality of panels and an actuator (not illustrated) that rotates the plurality of panels. The plurality of panels are arranged in a direction perpendicular to the axis of the air path 4, and rotation of the plurality of panels by the actuator opens and closes the air path 4. The shutter 2b and the shutter 3b are connected to the controller 10 by cable or by radio so as to be able to receive control signals from the controller 10. Since the air path 4 is closed by the shutter 2b and the shutter 3b in a case where a concentration of hydrogen gas as detected by the hydrogen gas sensor 7 is equal to or higher than the predetermined concentration, the hydrogen supply apparatus 1c do not continue to supply, to the interior, a gas mixture having a hydrogen gas concentration that is equal to or higher than the predetermined concentration. For this reason, the hydrogen supply apparatus 1c has a high level of safety.

Figure 9:
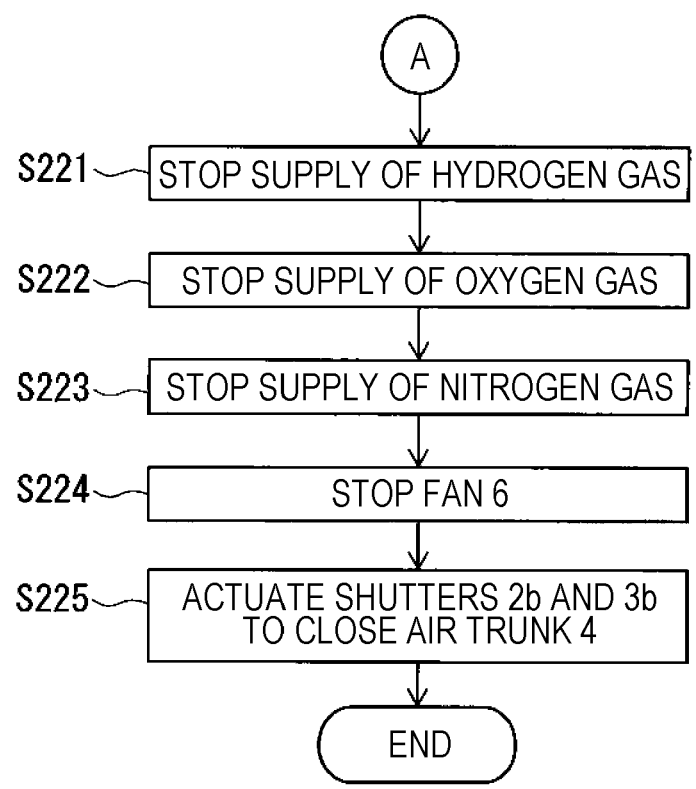
FIG. 9 is a flow chart showing an example of operation of the hydrogen supply apparatus of FIG. 8.

In a case where the result of the determination in step S114 is negative, the hydrogen supply apparatus 1c executes steps S221 to S225 shown in FIG. 9 instead of executing steps S201 to S204 shown in FIG. 3. Steps S221, S222, S223, and S224 are executed in a similar manner to steps S201, S202, S203, and S204, respectively. In step S225, the controller 10 controls the shutter 2b and the shutter 3b to close the air path 4 and ends the series of steps.

As shown in FIG. 10, the hydrogen supply apparatus 1d is configured such that the hydrogen gas supply source 9 includes an electrolytic device 17. The electrolytic device 17 produces hydrogen gas by electrolysis of water. In this case, the hydrogen gas supply source 9 further includes a container 18. The container 18 has water stored therein, and the container 18 is connected to the electrolytic device 17 so that water can be supplied to the electrolytic device 17. Hydrogen gas produced by the electrolytic device 17 is supplied to the air path 4 through the flow control device 8 and the mixer 20. The hydrogen supply apparatus 1d makes it possible to produce hydrogen gas by electrolysis of water and supply a mixture of the hydrogen gas and outdoor air to the interior even in an environment provided with no hydrogen gas supply infrastructure. Further, as compared with a case where a pressure tight case having high-pressure hydrogen stored therein is used as a hydrogen gas supply source, there is no need for a task of replacing hydrogen gas supply sources. In addition, since it is only necessary to produce hydrogen by electrolysis of water according to demand for hydrogen supply, it is not necessary to store hydrogen gas for a long period of time.

For example, the electrolytic device 17 has a water-containing electrolyte accommodated therein, and has an anode and a cathode immersed in the electrolyte. The electrolytic device 17 is electrically connected, for example, to a solar cell (not illustrated) and can generate a predetermined potential difference between the anode and the cathode under electric power generated by the solar cell. As a result, water can be electrolyzed. Of the electric power generated by the solar cell, a surplus of electric power over electric power demand from equipment other than the hydrogen supply apparatus 1d is used for the electrolytic device 17 to perform electrolysis of water. As the power source on which to operate the electrolytic device 17, a power source other than the solar cell may be utilized.

In the hydrogen supply apparatus 1d, nitrogen gas is supplied as a diluent gas to the mixer 20. The hydrogen supply apparatus 1d further includes a gas separator 16. The gas separator 16 separates, from air, nitrogen gas with which to dilute hydrogen gas. For this reason, the running costs of the hydrogen supply apparatus 1d are low.

The gas separator 16 has an internal space partitioned into a plurality of spaces, for example, by an oxygen enrichment membrane. The oxygen enrichment membrane is for example a hollow fiber membrane. A space in the internal space of the gas separator 16 located on an outer side of the oxygen enrichment membrane communicates with the mixer 20, and a space in the internal space of the gas separator 16 located on an inner side of the oxygen enrichment membrane is connected to the fourth supply port 12. The gas separator 16 is connected to an uptake port 14 through which to supply air to the gas separator 16. The uptake port 14 is disposed, for example, in the air path 4. In this case, since the hydrogen supply apparatus 1*d* includes the filter 3*a*, air having passed through the filter 3*a* and containing few foreign substances can be taken up through the uptake port 14. This makes adhesion of foreign substances to the oxygen enrichment membrane difficult and makes it possible to keep high efficiency of separation of nitrogen gas for a long period of time.

Of the air supplied into the gas separator 16 through the uptake port 14, oxygen gas flows toward the fourth supply port 12 through the oxygen enrichment membrane. Meanwhile, nitrogen gas flows toward the mixer 20 without passing through the oxygen enrichment membrane. In such a case where nitrogen gas is separated from air for use in dilution of hydrogen gas, only the flow rate of nitrogen gas needs to be controlled, so that the third flow control device 12*a* may be omitted.

The hydrogen supply apparatus 1*d* is suitable to being incorporated, for example, into a movable body. This is because it is difficult to continue to supply a movable body with hydrogen gas and nitrogen gas from external infrastructure. The hydrogen supply apparatus 1*d* is suitable in particular to being incorporated into a vehicle such as an automobile or a railroad vehicle. Further, the hydrogen supply apparatus 1*d* is suitable to being utilized in a system that produces hydrogen gas by utilizing electric energy obtained from renewable energy called "P2G (Power to Gas)" or in a building, such as a house, including equipment that produces hydrogen gas.

Figure 11:
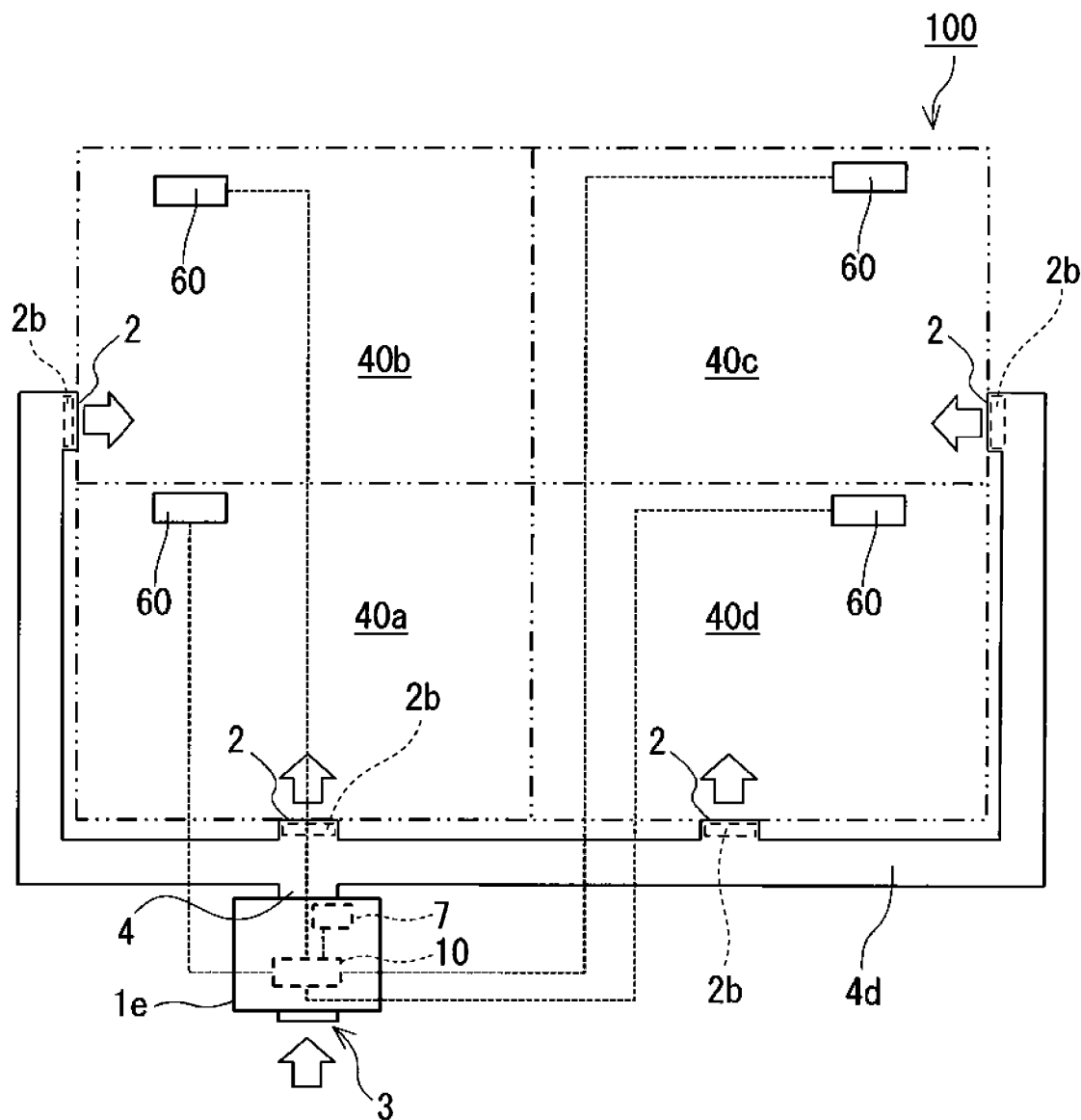
FIG. 11 is a diagram schematically showing still another example of a hydrogen supply apparatus of the present disclosure and an example of a hydrogen supply system of the present disclosure.

The hydrogen supply apparatus 1*a* may be modified to be like a hydrogen supply apparatus 1*e* shown in FIG. 11. The hydrogen supply apparatus 1*e* is configured in the same manner as the hydrogen supply apparatus 1*a* unless otherwise noted. Constituent elements of the hydrogen supply apparatus 1*e* which are identical to or correspond to those of the hydrogen supply apparatus 1*a* are given the same reference signs and are not described in detail below. The foregoing description of the hydrogen supply apparatuses 1*a*, 1 *b*, 1*c*, and 1*d* applies to the hydrogen supply apparatus 1*e* unless a technical contradiction arises.

In the hydrogen supply apparatus 1*e*, the air path 4 includes a downstream portion 4*d*. The downstream portion 4*d* has a plurality of outlets 2. There is no particular limitation on the number of outlets 2 that the downstream portion 4*d* has. As shown in FIG. 11, the downstream portion 4*d* has, for example, four outlets 2. A first area 40*a*, a second area 40*b*, a third area 40*c*, and a fourth area 40*d* are each provided with one outlet 2. This makes it possible to supply hydrogen gas together with outdoor air to the first area 40*a*, the second area 40*b*, the third area 40*c*, and the fourth area 40*d*. The first area 40*a*, the second area 40*b*, the third area 40*c*, and the fourth area 40*d* are each an indoor space. The first area 40*a*, the second area 40*b*, the third area 40*c*, and the fourth area 40*d* may each be partitioned from an outside of the area by a partition wall or a door or may each be connected to the outside of the area without being partitioned. In a case where the first area 40*a*, the second area 40*b*, the third area 40*c*, and the fourth area 40*d* are each not partitioned from the outside of the area, it is possible to supply hydrogen, for example, only to a region in one area where there is a low hydrogen concentration.

In the hydrogen supply apparatus 1*e*, the hydrogen gas sensor 7 is disposed, for example, upstream of the downstream portion 4*d* in the direction of flow of air. The hydrogen gas sensor 7 is typically disposed between the end 31 and the downstream portion 4*d*. As a result, for example, the concentrations of hydrogen gas in gas mixtures that are supplied from the plurality of outlets 2, respectively, can be detected with one hydrogen gas sensor 7, so that the concentrations of hydrogen gas can be efficiently detected.

The hydrogen supply apparatus 1*e* further includes, for example, a plurality of shutters 2*b* disposed in the downstream portion 4*d*. The shutters 2*b* of the hydrogen supply apparatus 1*e* are configured in the same manner as the shutters of the hydrogen supply apparatus 1*c*. Each of the plurality of shutters 2*b* is disposed in correspondence with one outlet 2. Further, each of the plurality of shutters 2*b* corresponds to one outlet 2 that is different from one outlet 2 to which another of the plurality of shutters 2*b* corresponds. As a result, a shutter 2*b* corresponding to an outlet 2 disposed in an area that does not need the supply of a gas mixture is closed under control of the controller 10, whereby the supply of a gas mixture to the area can be prevented.

In the hydrogen supply apparatus 1*e*, the controller 10 acquires or stores, for example, first information indicating the presence or absence of a human in the interior. When the first information indicates the presence of a human in the interior, the controller 10 controls the flow control device 8 to supply hydrogen gas to the air path 4. For example, when the first information indicates the presence of a human in any of the first, second, third, and fourth areas 40*a*, 40*b*, 40*c*, and 40*d*, the controller 10 controls the flow control device 8 to supply hydrogen gas to the air path 4.

On the other hand, when the first information indicates the absence of a human in the interior, the controller 10 controls the flow control device 8 to stop the supply of hydrogen gas to the air path 4 or keep hydrogen gas unsupplied to the air path 4. For example, when the first information indicates the absence of a human in any of the first, second, third, and fourth areas 40*a*, 40*b*, 40*c*, and 40*d*, the controller 10 controls the flow control device 8 to stop the supply of hydrogen gas to the air path 4. This makes it possible to avoid wasting hydrogen gas.

Assume a case where the first information indicates the presence of humans in the first area 40*a* and the second area 40*b* and indicates the absence of humans in the third area 40*c* and the fourth area 40*d*. In this case, the controller 10 controls the flow control device 8 to supply hydrogen gas to the air path 4. In addition, the controller 10 controls shutters 2*b* corresponding to outlets 2 disposed in the first area 40*a* and the second area 40*b* and thereby opens these shutters 2*b*. Meanwhile, the controller 10 controls shutters 2*b* corresponding to outlets 2 disposed in the third area 40*c* and the fourth area 40*d* and thereby closes these shutters 2*b*. As a result, a gas mixture containing hydrogen gas is supplied only from the outlets 2 disposed in the first area 40*a* and the second area 40*b*. It is desirable that the controller 10 control the flow control device 8 to supply hydrogen gas to the air path 4 at a flow rate consistent with the supply of the gas mixture to the first area 40*a* and the second area 40*b*. This makes it possible to efficiently utilize hydrogen gas.

As shown in FIG. 11, the hydrogen supply apparatus 1*e* can constitute a hydrogen supply system 100. The hydrogen supply system 100 includes the hydrogen supply apparatus 1*e* and a detector 60. The detector 60 detects, for example, the presence or absence of a human in the interior. In this case, the detector 60 is for example a human sensor. The detector 60 is for example an infrared sensor. The controller 10 acquires, as the first information, information indicating a result of detection yielded by the detector 60. The controller 10 is connected to the detector 60 by cable or by radio so as to be able to acquire information indicating a result of detection yielded by the detector 60.

For example, at least one detector 60 is disposed in each of the first, second, third, and fourth areas 40a, 40b, 40c, and 40d. This makes it possible to detect the presence or absence of a human in each of the first, second, third, and fourth areas 40a, 40b, 40c, and 40d.

The controller 10 further acquires, for example, second information indicating the position of a human in the interior, and controls the flow control device 8 on the basis of the second information to adjust the flow rate of hydrogen gas. The detector 60 further detects, for example, the position of a human in the interior. In this case, too, an infrared sensor can be used as the detector 60. For example, a plurality of infrared sensors are disposed in the interior, and the position of a human in the interior can be determined on the basis of the position information and detection result of an infrared sensor that has detected the presence of the human. Further, the detector 60 may be an infrared or ultrasonic distance sensor. In this case, the detector 60 can detect the position of a human on the basis of a detection result indicating the distance between the detector 60 and the human.

The controller 10 may acquire the first information from a predetermined information terminal, a server, or the control panel. For example, the controller 10 may acquire, as the first information, room-stay schedule information of a user of the interior as stored in the predetermined information terminal or the server or room-stay schedule information of a user of the interior as inputted to the control panel. In this case, when room-stay start time indicated by the room-stay schedule information has come, the controller 10 controls the flow control device 8 to start the supply of hydrogen gas to the air path 4. Further, at a predetermined point of time prior to the room-stay start time indicated by the room-stay schedule information, the controller 10 may control the flow control device 8 to start the supply of hydrogen gas to the air path 4. The predetermined point of time is for example thirty minutes before the room-stay start time. In this case, a user of the interior can suck in hydrogen gas upon entry into the interior.

The controller 10 may acquire the second information, for example, from a predetermined information terminal mounted with a GPS (global positioning system) module. In this case, the controller 10 may acquire, as the second information, positional information transmitted from the GPS module of an information terminal of a user of the interior.

In the hydrogen supply apparatus 1e, the controller 10 acquires, for example, third information that is biological information of a human in the interior, and controls the flow control device 8 on the basis of the third information to adjust the flow rate of hydrogen gas. In this case, the detector 60 detects, for example, biological information of a human in the interior. An example of biological information of a human is body temperature. In this case, a usable example of the detector 60 is an infrared sensor.

Figure 12:
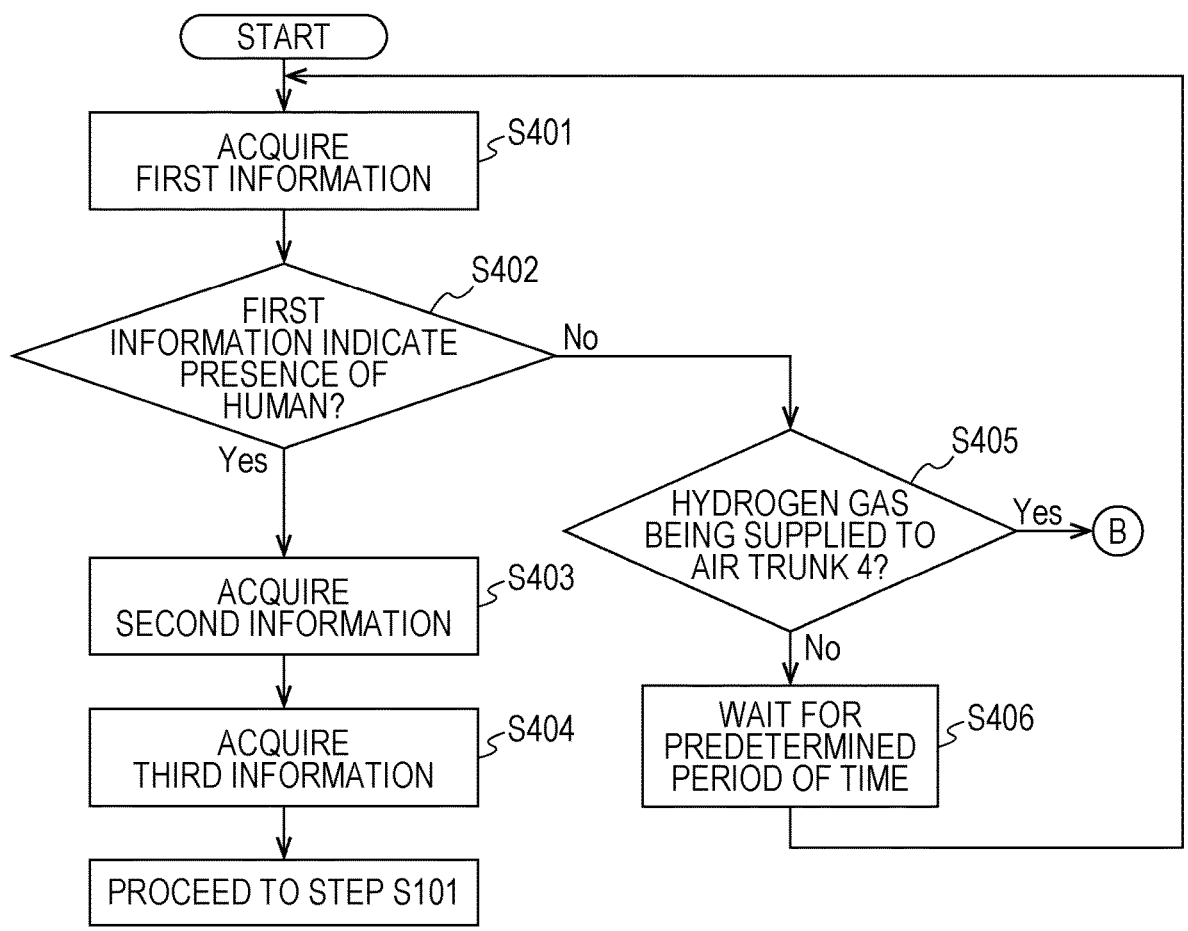
FIG. 12 is a flow chart showing an example of operation of the hydrogen supply apparatus shown in FIG. 11.
Figure 13:
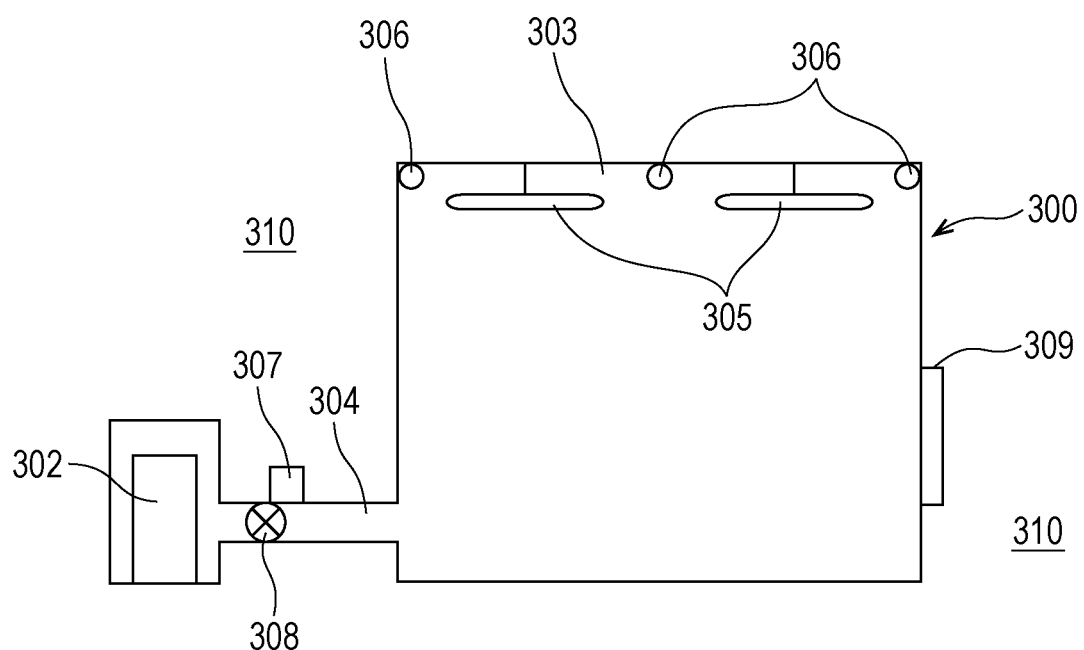
FIG. 13 is a diagram showing a conventional hydrogen supply system.

An example of operation of the hydrogen supply apparatus 1e is described. As shown in FIG. 12, in step S401, the controller 10 acquires first information. Next, the controller 10 proceeds to step S402 to determine whether the first information indicates the presence of a human in the interior. In a case where a result of the determination in step S402 is positive, the controller 10 proceeds to step S403 to acquire second information. Furthermore, the controller 10 proceeds to step S403 to acquire third information. After that, the controller 10 proceeds to step S101 shown in FIG. 2. For example, in step S102, the controller 10 sets a concentration of hydrogen gas with reference to the first information, the second information, and the third information. For example, in step S104, the controller 10 determines the flow rate of hydrogen gas on the basis of the first information, the second information, and the third information.

For example, in step S104, the controller 10 refers to the first information to determine the flow rate of hydrogen gas on the basis of the volume of an area among the first area 40a, the second area 40b, the third area 40c, and the fourth area 40d that indicates the presence of a human.

For example, in step S102, when the second information indicates that the position of a human in the interior is far away from an outlet 2, the controller 10 sets the concentration of hydrogen gas to a higher value than in a case where the second information indicates that the position of a human in the interior is close to an outlet 2.

For example, in step S102, in a case where the third information indicates a body temperature that is equal to or higher than a particular temperature, the controller 10 sets the concentration of hydrogen gas to a higher value than in a case where the third information indicates a body temperature that is lower than the particular temperature. The particular temperature ranges, for example, from 36.0° C. to 37.0° C. In the case of a comparatively high body temperature, it is conceivable that much active oxygen and many free radicals may be produced in the body. In this case, the amount of hydrogen gas that is sucked into the body is increased by increasing the flow rate of hydrogen gas, so that reduction by hydrogen of active oxygen and free radicals in the body can be promoted. On the other hand, in the case of a comparatively low body temperature, it is conceivable that little active oxygen and few free radicals may be produced in the body because of a small amount of activity as in the case of sleep. In this case, the amount of hydrogen gas that is used can be reduced by reducing the flow rate of hydrogen gas.

In a case where a result of the determination in step S402 is negative, the controller 10 proceeds to step S405 to determine whether hydrogen gas is being supplied to the air path 4. In a case where a result of the determination in step S405 is positive, the controller 10 executes steps S301 to S304 shown in FIG. 5. In a case where the result of the determination in step S405 is negative, the controller 10 proceeds to step S406 to wait for a predetermined period of time and then returns to step S401. Steps S402 and S403 may be performed at the same time as step S401, or each of steps S402 and S403 may be omitted.

The hydrogen supply apparatus 1e may be modified such that the air path 4 has one outlet 2. In this case, too, the controller 10 can acquire or store at least one of the first information, the second information, and the third information and, on the basis of these pieces of information, appropriately control a target of control such as the flow control device 8.

What is claimed is:
1. A hydrogen supply apparatus comprising:
   an air path having an inlet through which an air introduced into the hydrogen supply apparatus from an outside of the hydrogen supply apparatus and an outlet through which the air is exhausted to the outside of the hydrogen supply apparatus;

a fan that is disposed in the air path and produces a flow of the air from the inlet to the outlet;

a first pipe having an end that forms a first supply port through which to supply hydrogen gas to the air path;

a flow control device that is attached to the first pipe and adjusts a flow rate of the hydrogen gas; and a hydrogen gas sensor that is disposed downstream of the fan or the end in a direction of flow of the air and detects a concentration of the hydrogen gas in the air path, wherein the end is disposed between the fan and the outlet or between the fan and the inlet in the air path.

2. The hydrogen supply apparatus according to claim 1, further comprising a controller that controls the flow control device to keep a concentration of hydrogen gas at the outlet lower than a predetermined concentration.

3. The hydrogen supply apparatus according to claim 2, wherein in a case where a concentration of hydrogen gas as detected by the hydrogen gas sensor is equal to or higher than the predetermined concentration, the controller either controls the flow control device to stop supply of hydrogen gas to the air path or reduce a flow rate of hydrogen gas that is supplied to the air path or controls the fan to increase a flow rate of the air in the air path.

4. The hydrogen supply apparatus according to claim 2, wherein in a case where a concentration of hydrogen gas as detected by the hydrogen gas sensor is equal to or higher than the predetermined concentration, the controller controls the fan to increase a flow rate of the air in the air path and then controls the flow control device to stop supply of hydrogen gas to the air path or reduce a flow rate of hydrogen gas that is supplied to the air path.

5. The hydrogen supply apparatus according to claim 2, further comprising a temperature sensor disposed between the fan and the inlet in the air path, wherein in a case a temperature detected by the temperature sensor is equal to or higher than a particular temperature, the controller controls the flow control device and the fan to stop supply of hydrogen gas to the air path and stop the fan.

6. The hydrogen supply apparatus according to claim 1, wherein the air path has a vertically long air path through which to guide the flow of air from a lower position toward a higher position; and the end is disposed in the vertically long air path.

7. The hydrogen supply apparatus according to claim 1, further comprising a hydrogen gas supply source that supplies hydrogen gas to the first pipe.

8. The hydrogen supply apparatus according to claim 7, wherein the hydrogen gas supply source includes an electrolytic device that produces the hydrogen gas by electrolysis of water.

9. The hydrogen supply apparatus according to claim 1, further comprising a mixer that has a second supply port which is open to the air path, that is supplied with the hydrogen gas from the first pipe, and that dilutes the hydrogen gas with a diluent gas, wherein the hydrogen gas diluted in the mixer is supplied to the air path through the second supply port.

10. The hydrogen supply apparatus according to claim 9, wherein the mixer has a flow passage that allows passage of hydrogen gas having passed through the flow control device and a third supply port that is open to the flow passage and that serves to supply the diluent gas to the flow passage.

11. The hydrogen supply apparatus according to claim 9, wherein the diluent gas is a gas that is inert to hydrogen gas.

12. The hydrogen supply apparatus according to claim 11, wherein the diluent gas is nitrogen gas.

13. The hydrogen supply apparatus according to claim 12, further comprising a gas separator that is connected to the mixer and separates the nitrogen gas from air.

14. The hydrogen supply apparatus according to claim 1, further comprising a filter that is disposed in a first position between the inlet and the fan and between the inlet and the end in the air path, a second position between the outlet and the fan and between the outlet and the end in the air path, or in both the first position and the second position, that is made of an incombustible material, and that both transmits gases and captures foreign substances.

15. The hydrogen supply apparatus according to claim 1, further comprising a shutter that closes the air path and is disposed in at least one of a third position between the inlet and the fan and between the inlet and the end in the air path, and a fourth position between the outlet and the fan and between the outlet and the end in the air path, wherein in a case where a concentration of hydrogen gas as detected by the hydrogen gas sensor is equal to or higher than the predetermined concentration, the controller controls the shutter to close the air path.

16. The hydrogen supply apparatus according to claim 1, wherein the air path includes a downstream portion that has a plurality of outlets.

17. The hydrogen supply apparatus according to claim 1, wherein the air path includes a downstream portion that has a plurality of outlets, and the hydrogen gas sensor is disposed upstream of the downstream portion in the direction of flow of the air.

18. The hydrogen supply apparatus according to claim 2, wherein the controller acquires or stores first information indicating presence or absence of a human in the interior, and when the first information indicates the presence of a human in the interior, the controller controls the flow control device to supply hydrogen gas to the air path.

19. The hydrogen supply apparatus according to claim 18, wherein the controller further acquires second information indicating a position of the human in the interior, and controls the flow control device on the basis of the second information to adjust a flow rate of the hydrogen gas.

20. The hydrogen supply apparatus according to claim 2, wherein the controller acquires third information that is biological information of a human in the interior, and controls the flow control device on the basis of the third information to adjust a flow rate of the hydrogen gas.

\* \* \* \* \*